United States Patent
Savilahti et al.

(10) Patent No.: US 9,234,190 B2
(45) Date of Patent: Jan. 12, 2016

(54) METHOD FOR PRODUCING HYPERACTIVE TRANSPOSASE MUTANTS

(71) Applicant: Harri Savilahti, Helsinki (FI)

(72) Inventors: Harri Savilahti, Helsinki (FI); Tiina Rasila, Espoo (FI)

(73) Assignee: Harri Savilahti, Helsinki (FI)

( * ) Notice: Subject to any disclaimer, the term of this patent is extended or adjusted under 35 U.S.C. 154(b) by 0 days.

(21) Appl. No.: 14/404,411

(22) PCT Filed: May 30, 2013

(86) PCT No.: PCT/FI2013/050586
§ 371 (c)(1),
(2) Date: Nov. 26, 2014

(87) PCT Pub. No.: WO2014/013127
PCT Pub. Date: Jan. 23, 2014

(65) Prior Publication Data
US 2015/0147753 A1    May 28, 2015

(30) Foreign Application Priority Data

May 30, 2012 (FI) ..................... 20125586

(51) Int. Cl.
C12P 21/02 (2006.01)
C12N 9/12 (2006.01)
C12N 9/22 (2006.01)
C12Q 1/68 (2006.01)

(52) U.S. Cl.
CPC ............... *C12N 9/1241* (2013.01); *C12N 9/22* (2013.01); *C12Q 1/68* (2013.01); *C12Y 301/22* (2013.01); *C12Y 605/01* (2013.01)

(58) Field of Classification Search
None
See application file for complete search history.

(56) References Cited

PUBLICATIONS

Database Genbank [online] Mar. 15, 2005, Accession No. EHX94064, transposase [*Escherichia coli* DEC14D] [retrieved on Mar. 15, 2013]. Retrieved from the Internet: <URL: http://www.ncbi.nlm.gov/protein/EXH94064> & sequence alingment with SEQ ID No. 1.
Database Uniprot [online] Oct. 19, 2011, Accession No. G0FCG6, transposase [retrieved on Mar. 15, 2013]. Retrieved from the Internet: <URL: http://www.uniprot.org/uniprot/G0FCG6> & sequence alingment with SEQ ID No. 1.
Epicentre Hyper Mu MuA transposase [online brochure], Epicentre Biotechnologies (2005), [last modified Feb. 5, 2005] [retrieved on Mar. 18, 2013]. Retrieved from the Internet: <URL www.biomarket.cc/UpFiles/product/THM03210.pdf>.
International Search Report issued Sep. 9, 2013, in PCT International Application No. PCT/FI2013/050586.
Kim et al., "N-Terminal Domain-Deleted Mu Transposase Exhibits Increased Transposition Activity with Low Target Site Preference in Modified Buffers," J. Mol. Microbiol. Biotechnol. (2009), vol. 17, pp. 30-40.
Naigamwalla et al., "Mutations in domain IIIα of the Mu Transposase: Evidence Suggesting an Active Site Component which Interacts with the Mu-Host Junction," J. Mol. Biol. (1998), vol. 282, pp. 265-274.
Pajunen et al., "Universal platform for quantitative analysis of DNA transposition," Mobile DNA (2010), vol. 1, No. 24, pp. 1-14.
Rasila et al., "Flexibility in MuA Transposase Family Protein Structures: Functional Mapping with Scanning Mutagenesis and Sequence Alingment of Protein Homologues," PLoS ONE (May 2012), vol. 7, No. 5, e37922, pp. 1-20.
Rasila, T., Functional Mapping of Mu Transposition Machinery: MuA Protein Modification and Engineering for Hyperactivity, Doctoral disseration, 2013, University of Helsinki, Faculty of Biological and Environmental Sciences, Department of Biosciences, Division of Biochemistry and Biotechnology, ISBN: 978-952-10-8718-9.
Search Report issued Mar. 20, 2013, in Finnish Patent Application No. 20125586.

*Primary Examiner* — Jim Ketter
(74) *Attorney, Agent, or Firm* — Birch, Stewart, Kolasch & Birch, LLP

(57) ABSTRACT

The present invention provides a method for producing a hyperactive MuA transposase variant comprising at least one single-amino-acid change, the method comprising the steps of modifying the nucleic acid encoding wild type MuA transposase in at least one of the positions 59, 97, 160, 179, 233, 254, 258, 302, 335, 340, 345, 374, 447, 464, 478, 482, 483, 487, 495, 507, 539, 594 or 617 so that the modified nucleic acid encodes a MuA transposase variant comprising at least one single-amino-acid change in its amino acid sequence, wherein said single-amino-acid change results in higher enzyme activity of the variant when compared to the wild type MuA transposase. The present invention also provides hyperactive MuA transposases and kits comprising the same.

14 Claims, 6 Drawing Sheets

METHOD FOR PRODUCING HYPERACTIVE TRANSPOSASE MUTANTS

FIELD OF THE INVENTION

Figure 1:
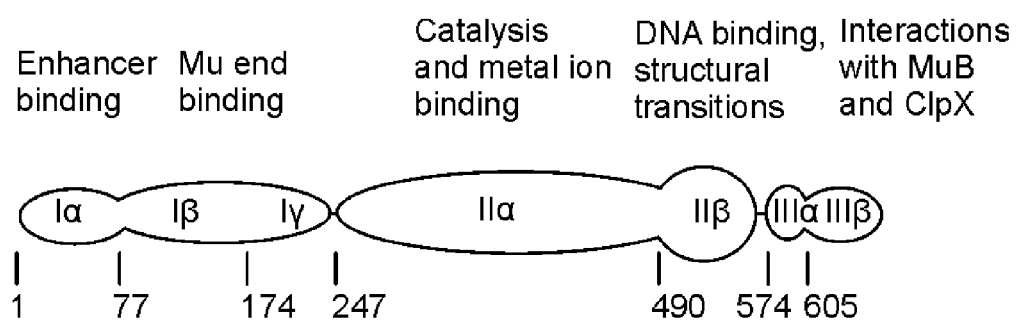

The present invention relates to the field of genetic engineering, particularly to the field of recombinant protein production. The present invention provides a method for producing a hyperactive MuA transposase variant comprising at least one single-amino-acid-change, the method comprising the steps of modifying the nucleic acid encoding wild type MuA transposase so that the modified nucleic acid encodes a MuA transposase variant comprising at least one single-amino-acid change in its amino acid sequence, wherein said single-amino-acid change results in higher enzyme activity of the variant protein when compared to the wild type MuA transposase. The present invention also provides hyperactive MuA transposases and kits comprising the same.

BACKGROUND OF THE INVENTION

Transposable genetic elements constitute a diverse group of discrete DNA segments with a capability of moving within and between genomes (1). They are abundant in all kingdoms of life and present in virtually every genome examined to date (1, 2). A wealth of data from sequenced genomes has implicated the fundamental importance of mobile DNA in shaping genomes during evolution (3-6). The increasing knowledge of DNA mobility mechanisms has facilitated the versatile use of transposable elements for research purposes and provided efficient tools for a variety of applications including genome-wide insertional mutagenesis, protein engineering, transgenesis, and gene therapy (7-9).

Phage Mu is a mobile DNA element encoding MuA transposase, the critical catalytic component of the mobilization machinery. MuA transposase belongs to the retroviral integrase superfamily of proteins. It catalyzes DNA cleavage and joining reactions via an initial assembly and subsequent structural transitions of a protein-DNA complex, known as the Mu transpososome, ultimately attaching transposon DNA into non-specific target DNA. The transpososome functions as a molecular DNA-modifying machine and has been used in a wide variety of molecular biology and genetics/genomics applications. It would be advantageous if the primary component of the Mu transpososome, the MuA transposase, could be modified for better performance with regard to the applications. Here, we have mutated MuA protein using random mutagenesis methods in order to identify MuA variants with enhanced transpositional activity. Initially, we generated a pool of randomly mutated MuA-expressing plasmid clones, and by screening approx. 60.000 clones identified several hundred clones expressing hyperactive MuA variants. The identification employed a genetic screen using a quantitative in vivo transposition assay. This quantitative assay is based on the mobilization of a reporter transposon inside *Escherichia coli* cells. In this assay, individual transposition events are scored as blue microcolonies (papillae) growing on otherwise whitish bacterial colonies. The mutant-phenotype-causing nucleotide changes were then identified by DNA sequencing for 92 MuA-variant-expressing clones. Subsequently, the identified nucleotide changes, translated as amino acid changes, were mapped onto the primary amino acid sequence of MuA transposase. A total of 47 changes were selected for further scrutiny. Corresponding amino acid changes were introduced individually into MuA. These single-amino-acid-change MuA variants were then analyzed by the papillation analysis for their transpositional activity. This way, we identified 33 single-substitution MuA variants, which generated more than 2-fold excess papillae in the assay relative to the wild type MuA. We further showed that enhanced transpositional activities identified in the in vivo papillation assay were largely recapitulated in two other assays relevant for MuA-based transposon applications, namely: (i) introduction of transpososomes into bacterial cells for genomic integration and (ii) generation of recombinant molecules by in vitro transposition. These assays were performed using purified proteins expressed in *Escherichia coli*. In addition, we showed that by combining two or three activity-enhancing amino acid changes, cumulative enhancement in the protein activity could be attained. Thus, by combining several beneficial amino acid changes within a single MuA polypeptide, it is possible to generate MuA transposase variants that possess a substantially enhanced transpositional activity.

Many mobile DNA elements transpose via a DNA intermediate. This group of elements includes bacterial and eukaryotic transposons as well as transposing bacteriophages such as phage Mu. This phage utilizes DNA transposition as an important step in its propagation cycle. Owing to its efficient DNA mobilization capacity in vivo (10) and the early development of an in vitro system (11), phage Mu has served as an important model system for DNA transposition studies in general (12). Mu encodes MuA transposase, which catalyzes the critical steps of transposition: (i) initial cleavages at the transposon-host boundaries (donor cleavage) and (ii) covalent integration of the transposon into the target DNA (strand transfer). These steps proceed via sequential structural transitions within a nucleoprotein complex, a transpososome (12-16), the core of which contains four MuA molecules and two synapsed transposon ends (17,18). In vivo, the critical MuA-catalyzed reaction steps also involve the phage-encoded MuB targeting protein, host-encoded DNA architectural proteins (HU and IHF), certain DNA cofactors (MuA binding sites and transpositional enhancer sequence), as well as stringent DNA topology (19). The critical reaction steps mimicking Mu transposition into external target DNA can be reconstituted in vitro using MuA transposase, 50 bp Mu R-end DNA segments, and target DNA as the only macromolecular components (18, 20). Such a minimal system has been instrumental for the detailed analyses on the molecular mechanisms of Mu transposition (21-23). A versatile use of the reaction series with custom-designed substrates has generated a wealth of tools for molecular biology applications (24-29) and produced novel strategies for genetics/genomics research (30-34).

MuA is a 75-kDa protein (663 amino acids) and can be divided into structurally and functionally defined major domains (I, II, III) and subdomains (Iα, Iβ, Iγ; IIα, IIβ; IIIα, IIIβ) (35-39) (see also FIG. 1). The N-terminal subdomain Iα promotes transpososome assembly via an initial binding to a specific transpositional enhancer sequence (40, 41). The specific DNA binding to transposon ends, crucial for the transpososome assembly, is mediated through amino acid residues located in subdomains Iβ and Iγ (37,38). Subdomain IIα contains the critical DDE-motif of acidic residues (D269, D336 and E392), which is involved in the metal ion coordination during the catalysis (42, 43). Subdomains IIβ and IIα participate in nonspecific DNA binding, and they appear important during structural transitions (17,43). Subdomain IIIα also displays a cryptic endonuclease activity, which is required for the removal of the attached host DNA following the integration of infecting Mu (44, 45). The C-terminal subdomain IIIβ is responsible for the interaction with the phage-encoded MuB protein, important in targeting transposition into distal target sites (46-49). This subdomain is also important in interacting with the host-encoded ClpX protein, a factor which remodels the transpososome for disassembly (50). While all MuA subdomains are required for efficient phage Mu transposition inside *Escherichia coli*, the terminal subdomains Iα and IIIβ become dispensable in certain in vivo and in vitro conditions with appropriately altered DNA substrates and/or suitably modified reaction milieu (51,52).

Here, we have employed random mutagenesis to generate substitutions in MuA. From thousands of MuA substitution variants, we screened hyperactive transposase mutants and identified amino acid changes responsible for the observed phenotypic change. A combination of several hyperactivity-causing changes had a cumulative effect on the protein activity.

SHORT DESCRIPTION OF THE DRAWINGS

FIG. 1. MuA is divided into structurally and functionally defined major domains (I, II, III) and subdomains (Iα, Iβ, Iγ; IIα, IIβ; IIIα, IIIβ).

Figure 2:
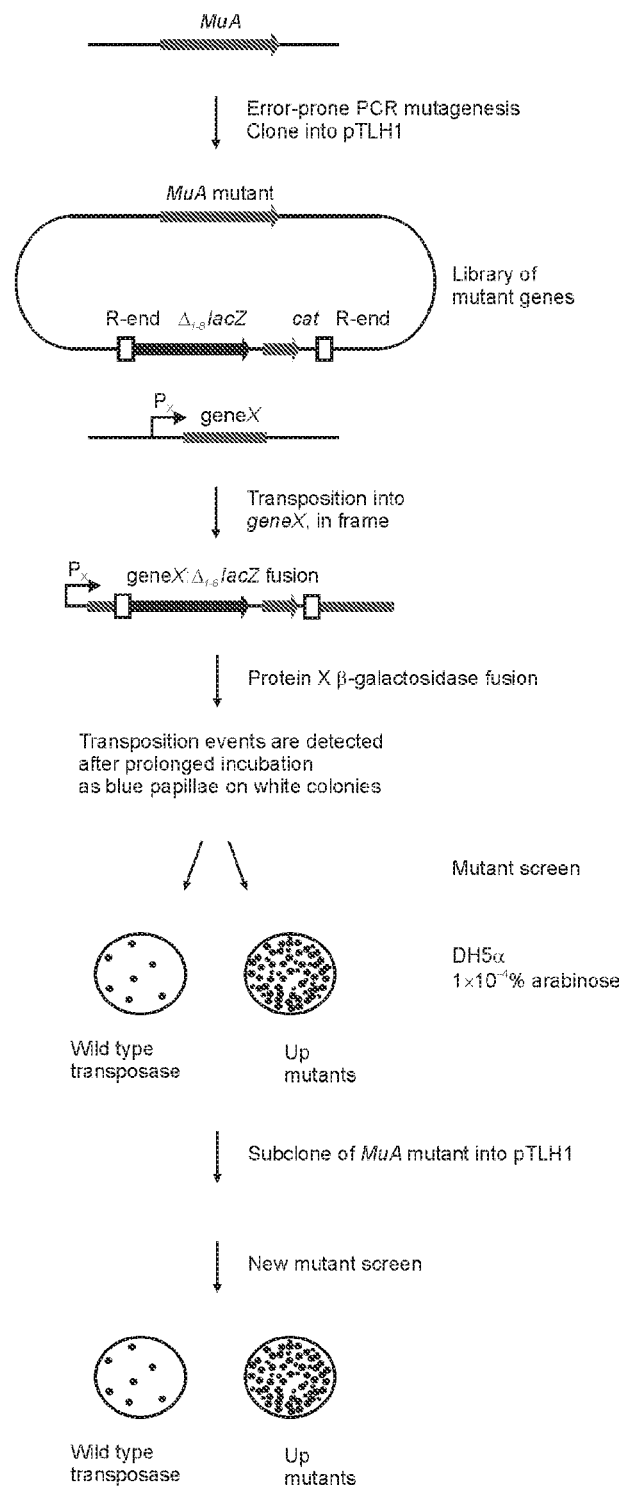

FIG. 2. Strategy to screen hyperactive MuA transposase variants. The random mutagenesis methods used and papillation assay utilized in the invention are both described in detail by Rasila et al., 2009, (53) and Pajunen et al., 2010 (51). In the papillation assay, phenotypically Lac⁻ *Escherichia coli* strain is transformed with a plasmid carrying a reporter transposon and encoding arabinose-inducible MuA transposase gene. Following expression of MuA, the reporter transposon is mobilized. Transposition into an expressed gene (geneX) in the correct orientation and reading frame generates a geneX:: lacZ gene fusion, expressing a protein fusion with a C-terminal β-galactosidase moiety. Such events can be detected as blue papillae in bacterial colonies growing on Xgal-containing indicator plates. This quantitative assay directly measures the activity of the MuA variant analyzed.

Figure 3:
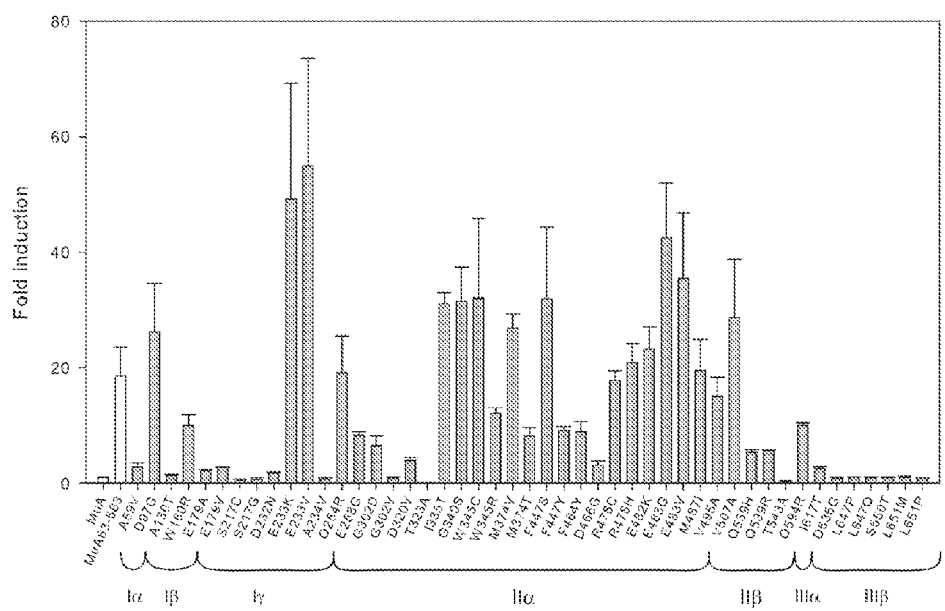

FIG. 3. Papillation assay results for 47 MuA variants. Each of these variants contain a single amino acid change generated by site-specific mutagenesis. The mean and standard deviations from three independent experiments are shown and represented as fold-increase over the wild type MuA protein activity. The data show at least two-fold increased activity for a total of 33 MuA variants.

Figure 4:
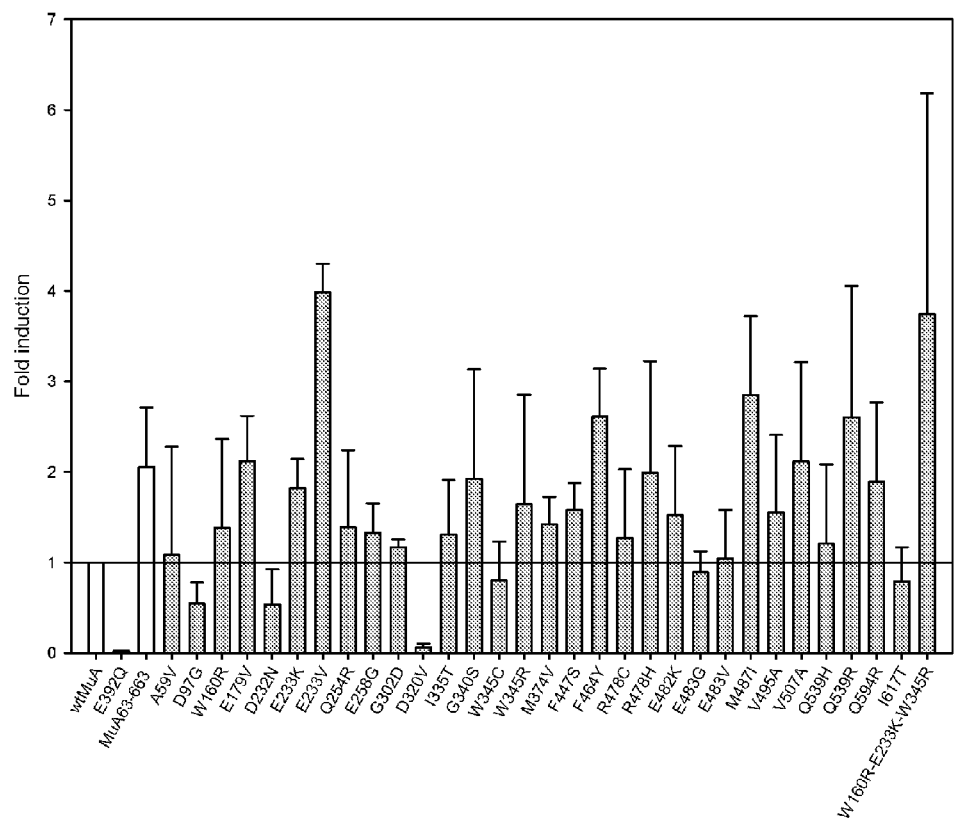

FIG. 4. Results from an assay measuring the proficiency of MuA variants in promoting gene delivery into bacterial genome. In this assay, an antibiotic resistance-encoding mini-Mu transposon is incubated with MuA protein to generate protein-DNA complexes called transpososomes. Subsequently, an aliquot from the transpososome-containing mixture is electroporated into *Escherichia coli* cells, where transpososomes catalyze genomic integration of the delivered transposon. The integrants are selected as growing colonies using the antibiotic resistance. The mean and standard deviation from three experiments are represented as fold-induction over the wild type MuA activity. As shown, most of the MuA variants analyzed portray an activity higher than that of the wild type protein.

Figure 5:
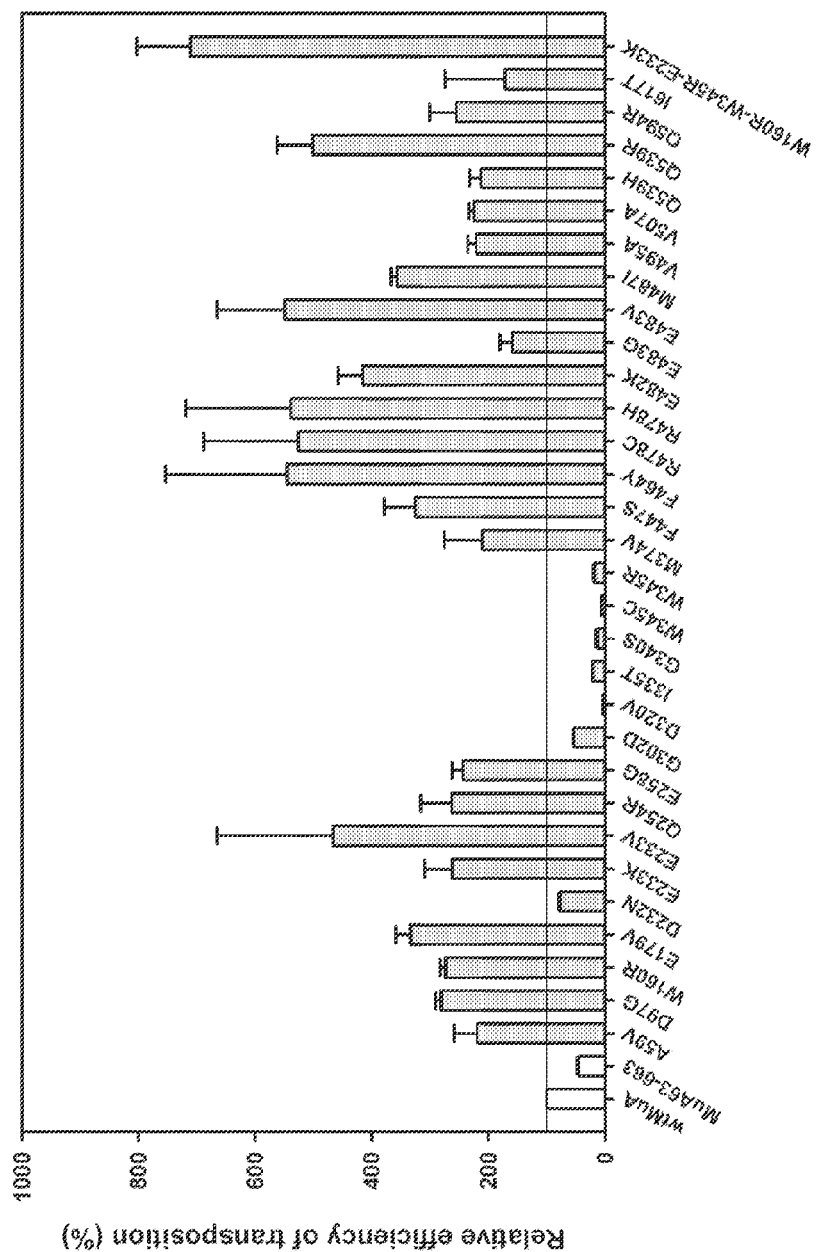

FIG. 5. Results from an assay measuring the proficiency of MuA variants in supporting in vitro transposon integration into an external plasmid target. In this assay, an antibiotic resistance-encoding mini-Mu transposon is incubated with MuA protein together with a selectable target plasmid. Following incubation, the reaction products are transformed into *Escherichia coli* cells. Transposon-containing target plasmids are then scored as growing bacterial colonies. Markers for both transposon and target are utilized in the selection. The efficiency of transposition is shown for each variant from triplicate experiments with mean and standard deviation indicated As shown, most MuA variants portray an enhanced activity in this assay.

Figures 6A, 6B:
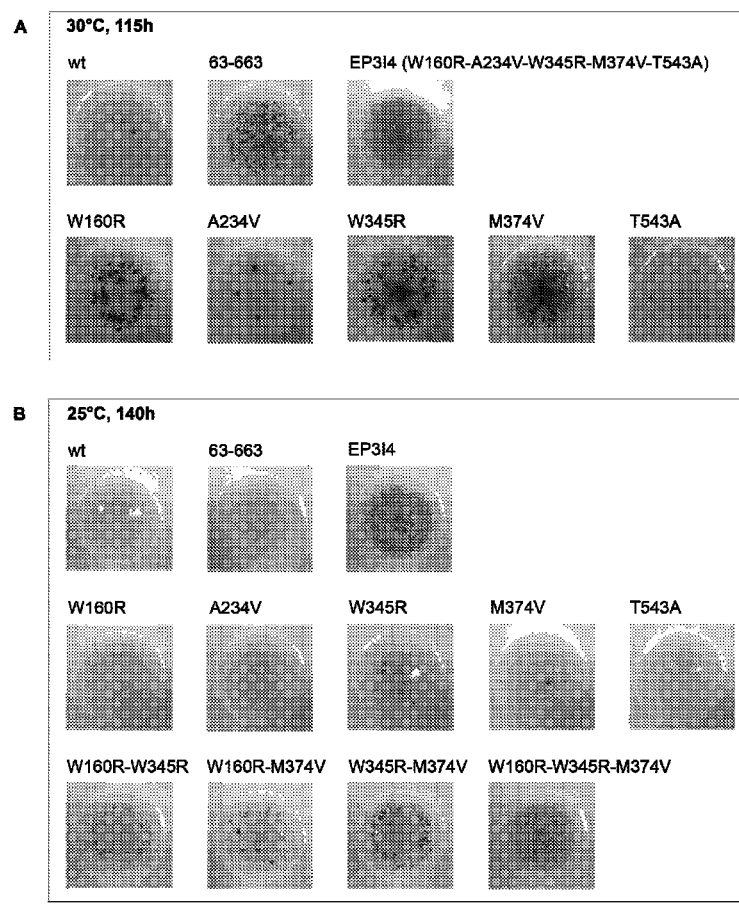

FIG. 6. Papillation assay results of MuA variants containing one or more amino acid changes. The standard papillation assay is performed at 30° C. for 115 h (FIG. 6A). Under these conditions, highly hyperactive MuA variants can not be quantitatively analyzed for their transpositional activity. However, such mutant variants can be compared quantitatively using lower temperature in the assay, e.g. 25° C. (FIG. 6B). As shown in the figure, combining several mutations has a cumulative effect on the protein activity.

DETAILED DESCRIPTION OF THE INVENTION

The term "transposon", as used herein, refers to a nucleic acid segment, which is recognized by a transposase or an integrase enzyme and which is an essential component of a functional nucleic acid-protein complex (i.e. a transpososome) capable of transposition. Minimal nucleic acid-protein complex capable of transposition in the Mu transposition system comprises four MuA transposase protein molecules and a pair of Mu end sequences that are able to interact with MuA. The term "transposase" as used herein refers to an enzyme, which is an essential component of a functional nucleic acid-protein complex capable of transposition and which is mediating transposition. The term "transposase" also refers to integrases from retrotransposons or of retroviral origin.

The expression "transposition reaction" used herein refers to a reaction wherein a transposon inserts into a target nucleic acid. Essential components in a transposition reaction are a transposon and a transposase or an integrase enzyme. The method and materials of the present invention are exemplified by employing in vitro Mu transposition (18, 20).

The term "hyperactive" relates herein to enzyme hyperactivity, i.e. the activity of a modified enzyme variant is considerably higher than the activity of the wild type enzyme.

The term "wild type MuA transposase" relates herein to the amino acid sequence as set forth in SEQ ID NO:1 or enzymatically active deletion variants thereof.

The present invention is directed to a method for producing a hyperactive MuA transposase variant comprising at least one single-amino-acid-change, the method comprising the steps of modifying the nucleic acid encoding wild type MuA transposase so that the modified nucleic acid encodes a MuA transposase variant comprising at least one single-amino-acid change at the amino acid positions of SEQ ID NO:1 selected from the group consisting of: 59, 97, 160, 179, 233, 254, 258, 302, 335, 340, 345, 374, 447, 464, 478, 482, 483, 487, 495, 507, 539, 594, and 617; and wherein said single-amino-acid change results in higher enzyme activity of the variant protein when compared to the wild type MuA transposase.

Preferably, the method is directed to the production of a MuA transposase nucleic acid modified to encode at least one of the single-amino-acid-changes selected from the group consisting of: A59V, D97G, W160R, E179V, E233K, E233V, Q254R, E258G, G302D, I335T, G340S, W345C, W345R, M374V, F447S, F464Y, R478H, R478C, E482K, E483G, E483V, M487I, V495A, V507A, Q539H, Q539R, Q594R and I617T.

As shown in FIGS. 3-5, MuA transposase variants comprising a single-amino-acid-change at position 233 are particularly preferable.

The present method may also comprise further step of expressing the modified nucleic acid in a host cell and preferably identifying those MuA variants the transposase activity of which is higher than the transposase activity of the wild type MuA. The identification step can be performed as a papillation assay disclosed below in the Experimental Section.

Another embodiment of the invention is a method for producing a hyperactive MuA transposase variant comprising at least two single-amino-acid-changes, the method comprising the steps of modifying the nucleic acid encoding wild type MuA transposase so that the modified nucleic acid encodes a MuA transposase variant comprising at least two single-amino-acid-changes at the amino acid positions of SEQ ID NO:1 selected from the group consisting of: 59, 97, 160, 179, 233, 254, 258, 302, 335, 340, 345, 374, 447, 464, 478, 482, 483, 487, 495, 507, 539, 594, and 617. Preferably, said MuA transposase variant produced comprises at least three single-amino-acid changes at the amino acid positions as described above. Advantageously, said two or three single-amino-acid-changes are in different domains of a MuA variant protein (see FIG. 1). For example, the Experimental Section discloses the production of a MuA transposase variant having the single-amino-acid-changes: W160R, E233K, and W345R.

In the present method, the nucleic acid encoding wild type MuA transposase is preferably modified by site-specific mutagenesis as described below in the Experimental Section. When the produced MuA variant comprises more than one single-amino-acid changes, the site-specific mutagenesis to produce the single-amino-acid changes may be done in one step or in a cumulative manner, wherein in the latter case the effect of each mutation to the cumulative activity of the variant is tested independently.

In one embodiment, the invention provides a hyperactive MuA transposase comprising at least one single-amino-acid-change at the amino acid positions of SEQ ID NO:1 selected from the group consisting of: 59, 97, 160, 179, 233, 254, 258, 302, 335, 340, 345, 374, 447, 464, 478, 482, 483, 487, 495, 507, 539, and 617, wherein said single-amino-acid change results in higher enzyme activity of the variant protein when compared to the wild type MuA transposase. For higher performance, the hyperactive MuA transposase may comprise two or three single-amino-acid-changes at said amino acid positions. Advantageously, said two or three single-amino-acid-changes are in different domains of a MuA variant protein (see FIG. 1).

Preferably, the hyperactive MuA transposase comprises at least one (or preferably two or three) of the single-amino-acid-changes selected from the group consisting of: A59V, D97G, W160R, E179V, E233K, E233V, Q254R, E258G, G302D, I335T, G340S, W345C, W345R, M374V, F447S, F464Y, R478H, R478C, E482K, E483G, E483V, M487I, V495A, V507A, Q539H, Q539R, and I617T.

In one preferred embodiment, the present invention provides a hyperactive MuA transposase comprising a single-amino-acid-change at position 233 of SEQ ID NO:1. More preferably, said hyperactive MuA transposase comprises or consists of the amino acid sequence as set forth in SEQ ID NO:2 with the single-amino-acid-change E233V. Another hyperactive MuA transposase disclosed by the present invention is the one comprising single-amino-acid-changes: W160R, E233K, and W345R, preferably comprising or consisting of the amino acid sequence as set forth in SEQ ID NO:3.

The present invention is further providing a kit for performing a transposase reaction, said kit comprising a hyperactive MuA transposase variant as defined above. Preferably, the kit comprises means for DNA sequencing. Said means can be selected from the group consisting of: buffers for performing transposition reaction, buffers for DNA sequencing, control DNA, transposase enzyme and DNA polymerase. The kit can be packaged in a suitable container and preferably it contains instructions for using the kit.

The publications and other materials used herein to illuminate the background of the invention, and in particular, to provide additional details with respect to its practice, are incorporated herein by reference. The present invention is further described in the following example, which is not intended to limit the scope of the invention.

Experimental Section

Materials and Methods
*Escherichia coli* Strains and Culture Conditions

DH10B (54) was used as a standard cloning host and DH5α (Invitrogen) for routine plasmid DNA isolation as well as for the papillation analysis. MuA transposase variants were expressed in BL21(DE3)(pLysS) (Novagen). MC1061 (55) was used as a recipient strain to score in vitro transposition reaction products. For standard use, bacteria were grown in Luria-Bertani (LB) medium as described (63) supplemented with ampicillin (Ap) and chloramphenicol (Cm) when required. Electrocompetent and standard competent cells were prepared as described by (56, 57), respectively.

Enzymes, Reagents, DNA Techniques and Plasmids.

Commercial proteins and reagents are listed in Table 1. $MuA_{E392Q}$ was purified as described (17). Oligonucleotides are listed in Table 2. Plasmid DNA was isolated using appropriate QIAGEN kits. Plasmids are described in Table 3. Standard DNA techniques were performed as described (56). Transposon Cat-Mu has been described (20). It was isolated from its carrier plasmid by BglII digestion and purified by anion exchange chromatography as described (20). DNA sequence determination was performed at the DNA sequencing facility of the Institute of Biotechnology (University of Helsinki) by using the BigDye terminator cycle sequencing kit and ABI 377 XL sequencer, both from Applied Biosystems.

Generation of MuA Mutant Libraries.

To construct MuA mutant libraries, error-prone PCR was performed using two different enzyme preparations: Taq DNA polymerase from Promega and Mutazyme II DNA polymerase mixture from Stratagene.

Taq DNA polymerase mutagenesis was performed essentially as described (65). Each standard PCR reaction (50 µl) contained 50 ng (12 fmol) plasmid pTLH2 (53) as a template, 0.3 µM each of the primers HSP492 and HSP493, 200 µM each dNTPs and 5 U Taq DNA polymerase in Taq DNA polymerase reaction buffer (10 mM Tris-HCl (pH 9.0 at 25° C.), 50 mM KCl, 1.5 mM $MgCl_2$, 0.1% (v/v) Triton X-100). Three independent amplifications were performed in which 0, 1, or 2 µl of mutagenic buffer (4 mM dTTP, 4 mM dCTP, 27.5 mM $MgCl_2$, and 2.5 mM $MnCl_2$) was included in the standard 50 µl reaction. PCR amplification employed initial 2 min at 94° C., 25 cycles of amplification (1 min at 94° C., 1 min at 59° C., 2.5 min at 72° C.), and final 10 min at 72° C. PCR products were purified using QIAquick PCR purification kit, digested with NcoI and EcoRI, and subjected to preparative electrophoresis on a 1.0% SeaPlaque GTG agarose in TAE buffer (56). The 2-kb MuA-encoding DNA segment (Gene Bank P07636), was isolated by QIAquick MinElute Gel Extraction Kit and ligated into the plasmid pTLH1 (51) digested with NcoI and EcoRI. Aliquots of the ligation mixtures were electroporated into DH10B cells. MuA variants containing plasmid clones were selected on LB-Ap-Cm plates (100 µg/ml Ap, 10 µg/ml Cm). From each ligation mixtures, approximately $6 \times 10^4$ colonies were pooled and, for plasmid preparation, grown in LB-Ap-Cm medium (100 µg/ml Ap, 10 µg/ml Cm) at 37° C. for 2 h.

Mutazyme II DNA polymerase mutagenesis was performed essentially as described (53) with pALH6 (53) as a template and HSP519/HSP492 as a primer pair for PCR amplification. Two independent mutant libraries were constructed with Mutazyme II DNA polymerase using five and ten amplification cycles. PCR products were extracted from a preparative agarose gel as described above and further amplified using Vent DNA polymerase in non-mutagenic reaction conditions as follows. Each amplification reaction (50 µl) contained approximately 10 ng of gel-purified PCR product as template, 0.5 µM each of the primers HSP492 and HSP493, 200 µM each dNTPs and 1 U Vent DNA polymerase (in ThermoPol reaction buffer: 20 mM Tris-HCl (pH 8.8 at 25° C.), 10 mM KCl, 10 mM $(NH_4)_2SO_4$, 4 mM $MgSO_4$, 0.1% (v/v) Triton X-100). PCR employed initial 5 min at 95° C., 25 cycles of amplification (45 s at 95° C., 1 min at 59° C., 2.5 min at 72° C.), and final 5 min at 72° C. PCR products were purified, digested, gel-isolated, cloned into pTLH1, and electroporated into DH10B cells as described above. Approximately $6 \times 10^4$ colonies were pooled and grown for DNA isolation as above.

Papillation Assay.

MuA mutant variants were assayed for their transpositional activity using an in vivo analysis that is based on transposon mobilization (51). This quantitative assay scores transposition events as blue microcolonies (papillae) growing on otherwise whitish *E. coli* colonies. It takes advantage of a plasmid, which contains a lacZ-containing reporter transposon and a cassette for arabinose-inducible MuA expression. Briefly, mutant plasmids were transformed into standard competent DH5α cells (50 µl), and the cells were plated onto LB agar plates supplemented with 100 µg/ml Ap, 20 µg/ml Cm, 0.05% lactose, 40 µg/ml Xgal, and $1 \times 10^{-4}$ 1% arabinose. The plates were normally incubated at 30° C. for 115 h.

To quantify highly hyperactive protein activities, plates were incubated at 25° C. for 140 h. For each data point, three representative colonies (diameter ~5 mm) were photographed using an Olympus (Tokyo, Japan) ColorView II digital camera attached to an Olympus SZX12 stereomicroscope equipped with Zeiss (Oberkochen, Germany) KL1500 LCD cold light source. The number of papillae in each colony was enumerated manually by the use of AnalySIS software (Soft Imaging System, Olympus).

Construction of Plasmids Encoding a MuA with Site-Specific Mutation.

Site-specific mutagenesis for each MuA variant was performed by PCR using a primer pair with one mutagenic primer and one non-mutagenic primer (Table 2). Each amplification reaction (50 µl) contained 100 ng pTLH4 as template, 0.5 µM each primer, 200 µM each dNTPs and 1U Phusion DNA polymerase (in Phusion HF buffer). An initial denaturation step (2 min at 98° C.) was followed by 10 cycles of amplification (30 s at 98° C., 1 min gradient 50-66° C., 7 min at 72° C.), and final 5 min at 72° C. Each amplified product was isolated from 0.5% SeaPlaque GTG agarose gel and purified using MinElute Gel exraction kit. Each product was treated with T4 polynucleotide kinase and circulated by ligation. The ligation products were transformed into *E. coli*, and each mutant plasmid was isolated. Mutant MuA variants were cloned into papillation vector pTLH1 cleaved with NcoI and KpnI. Sequences of MuA variants were confirmed by sequencing.

Production and Purification of Transposase Proteins.

The MuA variants were cloned into expression vector pET3d. Each respective protein variant was overexpressed and purified by the following modification of the described procedure (17). BL21(DE3)(pLysS) cells containing a MuA expression plasmid were grown in LB media (120 ml) containing antibiotics (100 µg/ml Ap and 35 µg/ml Cm) at 37° C. to an $OD_{600}$ of less than 1. Cells were then collected by centrifugation and shifted into LB medium (1.2 liters) supplemented with Ap (100 µg/ml). Cell propagation was continued at 28° C. to an $OD_{600}$ of 0.4-0.5. Protein expression was induced by the addition of IPTG (0.4 mM). Cells were harvested 2 h post-induction by centrifugation at 4° C., resuspended in an equal weight of 50 mM Tris-HCl, pH 8.0, 10% sucrose, 1 mM DTT, frozen in liquid nitrogen, and stored at −80° C. until used for protein purification.

Cell lysis and ammonium sulfate precipitation was performed as described (17), except that the precipitated MuA protein pellet was resuspended in HEDG plus 500 mM KCl (HEDG is 25 mM HEPES, pH 7.6, 0.1 mM EDTA, 1 mM DTT, 10% glycerol) to reach the original volume before precipitation. The protein solution was purified using phosphocellulose and hydroxylapatite columns as described (17) with the following modifications of the procedure. The protein solution was loaded onto 1.4 ml phosphocellulose (P11; Whatman) filled poly-prep column (Bio-Rad). The column was developed with a 7.4 vol gradient from 0.3-1.5 M KCl. Protein concentration of fractions was determined with the Bio-Rad Protein Assay using microtiter plate protocol based on the Bradford dye-binding procedure (58). The peak fractions were pooled and adjusted to conductivity of 10 mM $KPO_4$ and 500 mM KCl by addition HDG (HDG is 25 mM HEPES, pH 7.6, 1 mM DTT, 10% glycerol). The fraction was loaded onto a 0.45 ml hydroxyapatite (Macro-Prep Ceramic Hydroxyapatite Type I, Bio-Rad) packed in HR 5/2 (GE Healthcare Life Sciences) column in ÄKTApurifier system. The column was equilibrated in HDG plus 10 mM $KPO_4$ and 500 mM KCl. The column was developed with a 10 vol gradient from 10 mM-1M potassium phosphate in HDG plus 500 mM KCl. Peak fractions were pooled and dialyzed against HEDG plus 300 mM NaCl. Pooled fractions were frozen in liquid nitrogen and store at −80° C. Purity of protein preparations were confirmed by sodium dodecyl sulphate-polyacrylamide gel electrophoresis (SDS-PAGE) and nuclease assay. Protein concentration was determined spectrocopically using the following extinction coefficient $\epsilon_{1\ mg/ml}=1.58$.

Transpososomes.

Transpososomes were assembled as previously described (32). The assembly reaction (40 µl) contained 55 nM transposon DNA fragment, 245 nM MuA, 150 mN Tris-HCl pH 6.0%, 50% (v/v) glycerol, 0.025% (w/v) Triton X-100, 150 mM NaCl, and 0.1 mM EDTA. The reaction was carried out at 30° C. for 2 h. Transpososome preparations were frozen in liquid nitrogen and stored at −80° C. The formation of stable protein-DNA complexes with various transposase mutants were analysed by agarose/BSA/heparin gels as described (32).

In Vivo Chromosomal Integration of Mini-Mu Transposon.

Genomic integration activity into *Escherichia coli* chromosome was determined by the following modification of the described procedure (32). The transpososome assembly reaction mixture was diluted 1:8 with water and individual aliquots of 1 µl were electroporated into electrocompetent MC1061 cells (25 µl).

In Vitro Transposition Reactions and Biological Selection of Integrants.

Transposition activity was determined by in vitro transposition reaction (24). Standard reactions (25 μl) contained 0.5 pmol transposon DNA, 500 ng (0.4 pmol) pUC19 target DNA, 2.7 pmol (0.22 μg) MuA variant, 25 mM Tric-HCl, pH 8.0, 100 μg/ml BSA, 15% (w/v) glycerol, 0.05% (w/v) Triton X-100, 126 mM and 10 mM $MgCl_2$. Reactions were carried out for 1 h at 30° C. and stopped by freezing in liquid nitrogen. Following addition of 0.3 vol loading dye (0.1% bromophenol blue, 2.5% SDS, 50 mM EDTA, 25% Ficoll 400), transposition reaction products were analyzed by electrophoresis on a 0.8% SeaKem LE agarose gel in 1×TAE buffer (56). For biological selection of integrants, 5 μl of the transposition reaction products was transformed into competent E. coli cells (56).

Results

The Mu transposition system can be exploited in many types of molecular biology and genetic/genomics applications (20, 24-31), including gene delivery into the genomes of gram-negative and gram-positive bacteria as well as those of yeast and mammalian cells (32-34). In each application, the efficiency of transposon integration into target DNA is critical, and therefore it would be beneficial if more efficient insertion reaction could be reconstituted. Previous studies with other transposons have indicated that it is possible to generate enhanced transpositional activities by mutating the critical component of the integration apparatus, the transposase (59-62). In this study we set out to search for hyperactive MuA variants. For that we employed two random mutagenesis methods both described in detail by Rasila et al. (2009) (53, see also FIG. 2). With these methods, the critical mutagenesis parameters were adjusted with the aim to induce on the average at least one amino acid change within the protein. We used five different mutagenesis protocolls (three with Taq method and two with Mutazyme method) in order to generate a reasonable spectrum of different mutations and attain a reasonable mutation frequency. Following the mutagenesis phase, MuA genes were cloned as a pool into the plasmid pTLH1 for the analysis of transpositional activity. The activity measurement (so-called papillation assay) is based on the in vivo mobilization of a lacZ-containing reporter transposon. In the assay individual transposition events are scored as blue microcolonies (papillae) growing within otherwise whitish bacterial colonies (FIG. 2). The assay is quantitative and allows the screening of hypoactive as well as hyperactive transposase variants (51).

We screened approx. 60.000 individual MuA mutant variants, and from these variants identified 92 clones with an increased transpositional activity. These clones were subjected to sequence analysis to identify nucleotide changes. The changes were evaluated in translation and those generating an amino acid change were mapped onto the MuA primary amino acid sequence. This procedure generated a map of mutations potentially implicated in enhanced transpositional activity. Of these amino acid changes, a total of 47 changes were individually introduced in MuA. These substitution mutants were then analyzed for their transpositional activity using the papillatioin assay (FIG. 2). The results (FIG. 3) show at least two-fold increased activity for a total of 33 MuA variants.

We next purified 30 MuA variants to study them in applicationally relevant assays. First, we assayed their proficiency in promoting gene delivery into bacterial genome. As shown in FIG. 4, most of the MuA variants portrayed an activity higher than that of the wild type MuA. Second, we analyzed the proficiency of protein variants to support in vitro transposon integration into an external plasmid target. As shown in FIG. 5, most MuA variants portrayed enhanced activities in this assay. Taken together, in vivo results are largely recapitulated by both of the assays used.

Subsequently, we engineered two or three critical mutations into MuA (FIG. 6). The results indicate that each respective mutation combination portrays a higher activity than any of its single-mutation counterpart, thus indicating cumulative effects. Thus, it is possible to produce highly active MuA variants by combining critical amino acid changes into one polypeptide (see also Table 4).

TABLE 1

Proteins, reagents, and materials

| Protein/reagent/material | Supplier |
|---|---|
| Restriction endonucleases | New England Biolabs |
| Calf intestinene phosphatase (CIP) | Finnzymes |
| T4 polynucleotide kinase | New England Biolabs |
| T4 DNA ligase | New England Biolabs |
| Taq DNA polymerase | Promega |
| Mutazyme II DNA polymerase | Stratagene |
| Vent DNA polymerase | New England Biolabs |
| DyNAzyme II DNA polymerase | Finnzymes |
| Phusion DNA polymerase | Finnzymes |
| Ampicillin | Sigma |
| Chloramphenicol | Sigma |
| Isopropyl-β-D-thiogalactopyranoside (IPTG) | Fermentas |
| 5-bromo-4-chloro-3-indolyl-β-D-galactopyranoside (Xgal) | AppliChem Gmb H |
| Lactose | BDH/VWR International |
| Arabinose | Sigma |
| Phosphocellulose | Whatman |
| Hydroxyapatite | Bio-Rad |
| Poly-Prep columns | Bio-Rad |
| HR 5/2 column | GE Healthcare Life Sciences |
| Bio-Rad Protein Assay | Bio-Rad |
| GelCode ® Blue Stain Reagent | Pierce |
| Triton X-100 | Fluka |
| Glycerol | BDH |

TABLE 2

Oligonucleotides

| Oligonucleotide | Sequence 5'-3' | Comment |
|---|---|---|
| HSP570 | GATCGCCGGTACCAT (SEQ ID NO: 4) | KpnI-restriction site w HSP571, can be inserted at BamHI/BglII site |
| HSP571 | GATCATGGTACCGGC (SEQ ID NO: 5) | KpnI-restriction site w HSP570, can be inserted at BamHI/BglII site |

TABLE 2-continued

Oligonucleotides

| Oligonucleotide | Sequence 5'-3' | Comment |
|---|---|---|
| HSP583 | AGGGCGGCTGCACTTG (SEQ ID NO: 6) | MuA mutant W160R (tgg > agg) 5' PCR primer |
| HSP584 | GTCAGGCTTCGCAAACTTC (SEQ ID NO: 7) | MuA 3' PCR primer aa160 downstream |
| HSP585 | TAATGGTTGTTGCCTGTCGTG (SEQ ID NO: 8) | MuA mutant A234V (gca > gta) 5' PCR primer |
| HSP586 | CCTCGTCCAGTTGCTGAATC (SEQ ID NO: 9) | MuA 3' PCR primer aa234 downstream |
| HSP587 | AGGCTGACGGGAGGCG (SEQ ID NO: 10) | MuA mutant W345R (tgg > agg) 5' PCR primer |
| HSP588 | TTTATTCGCAGCACCACGGG (SEQ ID NO: 11) | MuA 3' PCR primer aa345 downstream |
| HSP589 | GCGGTTTATTGCTACACCCTG (SEQ ID NO: 12) | MuA mutant T543A (acg > gcg) 5' PCR primer |
| HSP590 | GCTGTGTAGCTGCTGCG (SEQ ID NO: 13) | MuA 3' PCR primer aa543 downstream |
| HSP591 | GTAACGCCAGCGATTCCC (SEQ ID NO: 14) | MuA mutant D97G (gat > ggt) 5' PCR primer |
| HSP592 | CCCATTTGCTCCACAGTGC (SEQ ID NO: 15) | MuA 3' PCR primer aa97 downstream |
| HSP593 | TGGCAATGGTTGTTGCCTGTC (SEQ ID NO: 16) | MuA mutant E233V (gag > gtg) 5' PCR primer |
| HSP594 | CGTCCAGTTGCTGAATCCG (SEQ ID NO: 17) | MuA 3' PCR primer aa233 downstream |
| HSP595 | TTGTTGTGACTCGCTACGGTATC (SEQ ID NO: 18) | MuA mutant D320V (gat > gtt) 5' PCR primer |
| HSP596 | CCATGAACGAGAGGCGAATTG (SEQ ID NO: 19) | MuA 3' PCR primer aa320 downstream |
| HSP597 | GCTCGCTACGGTATCCCG (SEQ ID NO: 20) | MuA mutant T323A (act > gct) 5' PCR primer |
| HSP598 | CACAACATCCATGAACGAGAGG (SEQ ID NO: 21) | MuA 3' PCR primer aa323 downstream |
| HSP599 | AGTGCTGCGAATAAATGGC (SEQ ID NO: 22) | MuA mutant G340S (ggt > agt) 5' PCR primer |
| HSP600 | ACGGGTGTTATCAATGGTGATG (SEQ ID NO: 23) | MuA 3' PCR primer aa340 downstream |
| HSP601 | CCTGACGGGAGGCGCG (SEQ ID NO: 24) | MuA mutant W345C (tgg > tgc) 5' PCR primer |
| HSP602 | CATTTATTCGCAGCACCACGG (SEQ ID NO: 25) | MuA 3' PCR primer aa345 downstream |
| HSP603 | ATGATGATGTTTTCGAGCGTG (SEQ ID NO: 26) | MuA mutant F464Y (ttt > tat) 5' PCR primer |
| HSP604 | ACGAGAGTTTGCCCCCG (SEQ ID NO: 27) | MuA 3' PCR primer aa464 downstream |
| HSP605 | GTGTTTTCGAGCGTGAATACG (SEQ ID NO: 28) | MuA mutant D466G (gat > ggt) 5' PCR primer |
| HSP606 | CATCAAACGAGAGTTTGCCCC (SEQ ID NO: 29) | MuA 3' PCR primer aa466 downstream |
| HSP607 | GACAAAAACGGATGCTGTTACTG (SEQ ID NO: 30) | MuA mutant E483G (gaa > gga) 5' PCR primer |

TABLE 2 -continued

Oligonucleotides

| Oligonucleotide | Sequence 5'-3' | Comment |
|---|---|---|
| HSP608 | CTTCGGTTGGCTTACGCAC (SEQ ID NO: 31) | MuA 3' PCR primer aa483 downstream |
| HSP609 | ACTGTTACTGCCTGCCGAG (SEQ ID NO: 32) | MuA mutant M487I (atg > ata) 5' PCR primer |
| HSP610 | ATCCGTTTTTGTTCTTCGGTTGG (SEQ ID NO: 33) | MuA 3' PCR primer aa487 downstream |
| HSP611 | CGAACGTTTCACGCAAAGGC (SEQ ID NO: 34) | MuA mutant V495A (gtg > gcg) 5' PCR primer |
| HSP612 | CCGCCTCGGCAGGCAG (SEQ ID NO: 35) | MuA 3' PCR primer aa495 downstream |
| HSP613 | CTGGCGGCTCCCTTAAAGG (SEQ ID NO: 36) | MuA mutant V507A (gtt > gct) 5' PCR primer |
| HSP614 | CTTTAAGCGTAAACTCGCCTTTG (SEQ ID NO: 37) | MuA 3' PCR primer aa507 downstream |
| HSP615 | GAATGGACGCGCTGGAAGTTG (SEQ ID NO: 38) | MuA mutant Q594R (caa > cga) 5' PCR primer |
| HSP616 | GTTTCTGCGCCTTAATGGCTG (SEQ ID NO: 39) | MuA 3' PCR primer aa594 downstream |
| HSP617 | TGGCGTTATTGCTGAGACAAG (SEQ ID NO: 40) | MuA mutant A59V (gcg > gtg) 5' PCR primer |
| HSP618 | CTTTCGCTTCAACAGGTAAAGAG (SEQ ID NO: 41) | MuA 3' PCR primer aa59 downstream |
| HSP619 | ACTTTTGCGACCGTTGCAGG (SEQ ID NO: 42) | MuA mutant A130T (gct > act) 5' PCR primer |
| HSP620 | CGTTTTCGTTGAAATCCCCTGG (SEQ ID NO: 43) | MuA 3' PCR primer aa130 downstream |
| HSP621 | CATTTGACGAGGATGCCTGG (SEQ ID NO: 44) | MuA mutant E179A (gaa > gca) 5' PCR primer |
| HSP622 | CACTTTTGTGAACATTGCGACG (SEQ ID NO: 45) | MuA 3' PCR primer aa179 downstream |
| HSP623 | TATTTGACGAGGATGCCTGGC (SEQ ID NO: 46) | MuA mutant E179V (gaa > gta) 5' PCR primer |
| HSP624 | GGCGAACTGTGGAACACCTGG (SEQ ID NO: 47) | MuA mutant Q245R (cag > cgg) 5' PCR primer |
| HSP625 | GCTGTGCCGGTATCAGATGC (SEQ ID NO: 48) | MuA 3' PCR primer aa254 downstream |
| HSP626 | AAAGAACAAAAACGGATGCTG (SEQ ID NO: 49) | MuA mutant E482K (gaa > aaa) 5' PCR primer |
| HSP627 | GGTTGGCTTACGCACAATC (SEQ ID NO: 50) | MuA 3' PCR primer aa482 downstream |
| HSP628 | TACAAAAACGGATGCTGTTACTGC (SEQ ID NO: 51) | MuA mutant E483K (gaa > gga) 5' PCR primer |
| HSP629 | TCTACACAGCACGGTTTATTGC (SEQ ID NO: 52) | MuA mutant Q539H (cag > cat) 5' PCR primer |
| HSP630 | TGCTGCGGATCAAACCTGAC (SEQ ID NO: 53) | MuA 3' PCR primer aa539 (2nd nucleotide) downstream |
| HSP631 | GGCTACACAGCACGGTTTATTG (SEQ ID NO: 54) | MuA mutant Q539R (cag > cgg) 5' PCR primer |
| HSP632 | GCTGCGGATCAAACCTGACC (SEQ ID NO: 55) | MuA 3' PCR primer aa539 (1st nucleotide) downstream |

TABLE 2 -continued

Oligonucleotides

| Oligonucleotide | Sequence 5'-3' | Comment |
|---|---|---|
| HSP633 | CTGTTGGTATTTTCCGGCCTTC (SEQ ID NO: 56) | MuA mutant I617T (att > act) 5' PCR primer |
| HSP634 | TTCGTGATTCTGGTGCTGC (SEQ ID NO: 57) | MuA 3' PCR primer aa617 downstream |
| HSP635 | CGAATCATTCGCTGGATATTC (SEQ ID NO: 58) | MuA mutant L647P (ctg > ccg) 5' PCR primer |
| HSP636 | GATATTCATCACGCTCAGTTTC (SEQ ID NO: 59) | MuA 3' PCR primer aa647 downstream |
| HSP637 | AGAATCATTCGCTGGATATTC (SEQ ID NO: 60) | MuA mutant L647Q (ctg > cag) 5' PCR primer |
| HSP638 | ACGCTGGATATTCTGGAACAG (SEQ ID NO: 61) | MuA mutant S650T (tcg > atg) 5' PCR primer |
| HSP639 | ATGATTCAGATATTCATCACGCTC (SEQ ID NO: 62) | MuA 3' PCR primer aa650 downstream |
| HSP640 | ATGGATATTCTGGAACAGAACAG (SEQ ID NO: 63) | MuA mutant S651M (ctg > atg) 5' PCR primer |
| HSP641 | CGAATGATTCAGATATTCATCACG (SEQ ID NO: 64) | MuA 3' PCR primer aa651 (starting 650) downstream |
| HSP642 | CGGATATTCTGGAACAGAACAG (SEQ ID NO: 65) | MuA mutant S651P (ctg > ccg) 5' PCR primer |
| HSP643 | GCGAATGATTCAGATATTCATCAC (SEQ ID NO: 66) | MuA 3' PCR primer aa651 (1st nucleotide) downstream |
| HSP644 | TGTATTCCCTCCCGTGCCACG (SEQ ID NO: 67) | MuA mutant S217C (agt > tgt) 5' PCR primer |
| HSP645 | CCAGCCATGCTCGCGGG (SEQ ID NO: 68) | MuA 3' PCR primer aa217 downstream |
| HSP646 | GGTATTCCCTCCCGTGCCACG (SEQ ID NO: 69) | MuA mutant S217G (agt > ggt) 5' PCR primer |
| HSP647 | AACGAGGCAATGGTTGTTGC (SEQ ID NO: 70) | MuA mutant D232N (gac > aac) 5' PCR primer |
| HSP648 | CAGTTGCTGAATCCGGCG (SEQ ID NO: 71) | MuA 3' PCR primer aa232 downstream |
| HSP649 | GACACCTGGACGCCATGC (SEQ ID NO: 72) | MuA mutant E258G (gaa > gga) 5' PCR primer |
| HSP650 | CCACAGTTCGCTGCTGTG (SEQ ID NO: 73) | MuA 3' PCR primer aa258 downstream |
| HSP651 | ACTGGCGCTGCGATGTG (SEQ ID NO: 74) | MuA mutant G302D (ggc > gac) 5' PCR primer |
| HSP652 | CCAGAATTTTTCGGGTTTTCACATCC (SEQ ID NO: 75) | MuA 3' PCR primer aa302 downstream |
| HSP653 | TCTGGCGCTGCGATGTG (SEQ ID NO: 76) | MuA mutant G302V (ggc > gtc) 5' PCR primer |
| HSP654 | CGCACTGGACAAGCGTTG (SEQ ID NO: 77) | MuA mutant M374T (atg > acg) 5' PCR primer |
| HSP655 | TTTTCGCCCCCATCAGTAAAAAC (SEQ ID NO: 78) | MuA 3' PCR primer aa374 downstream |
| HSP656 | ACAATGCCAGAACAGGCCGTG (SEQ ID NO: 79) | MuA mutant F447Y (ttc > tac) 5' PCR primer |
| HSP657 | ACATCGCCACACCTTCGGC (SEQ ID NO: 80) | MuA 3' PCR primer aa447 downstream |

TABLE 2 -continued

Oligonucleotides

| Oligonucleotide | Sequence 5'-3' | Comment |
|---|---|---|
| HSP658 | TGTAAGCCAACCGAAGAACAA (SEQ ID NO: 81) | MuA mutant R478C (cgt > tgt) 5' PCR primer |
| HSP659 | CACAATCGTTCTGGCGTATTC (SEQ ID NO: 82) | MuA 3' PCR primer aa478 downstream |
| HSP660 | ATAAGCCAACCGAAGAACAAAAACG (SEQ ID NO: 83) | MuA mutant R478H (cgt > cat) 5' PCR primer |
| HSP661 | GCACAATCGTTCTGGCGTATTC (SEQ ID NO: 84) | MuA 3' PCR primer aa478 downstream |
| HSP662 | GTGATGAATACGAAACTGAGCG (SEQ ID NO: 85) | MuA mutant D636G (gat > ggt) 5' PCR primer |
| HSP663 | CACGCTCCTGATTCTTCACC (SEQ ID NO: 86) | MuA 3' PCR primer aa636 downstream |

TABLE 3

Plasmids

| Plasmid | Relevant characteristics | Reference |
|---|---|---|
| pTLH1 | pBADHisA derivative carrying $\Delta_{1-8}$lacZ cat transposon with Mu R-ends; Ap$^R$, Cm$^R$ | (51) |
| pTLH2 | pBADHisA derivative expressing MuA$_{wt}$ and carrying lacZα with pLAC; Ap$^R$ | (53) |
| pTLH4 | MuA$_{wt}$ from pLHH4 cloned between NcoI and KpnI sites of pTLaH1 | This work |
| pALH6 | MuA$_{wt}$ from pMK591 cloned between NcoI and BamHI sites of pBADHisA; Ap$^R$ | (53) |
| pLHH4 | pBADHisA derivative expressing MuA$_{wt}$ transposase and carrying $\Delta_{1-8}$lacZ cat transposon with Mu R-ends; Ap$^R$, Cm$^R$ | (51) |
| pET3d | Ap$^R$ | Novagen |
| pTLaH1 | KpnI site cloned into BamHI site of pET3d; Ap$^R$ | This work |
| pTLH4 | MuA$_{wt}$ from pLHH4 cloned between NcoI and KpnI sites of pTLaH1 | This work |
| pUC19 | Ap$^R$ | New England Biolabs |

TABLE 4

Enhancement of transposition frequency by various mutation combinations.

| Mutations | Number of papillae[a] |
|---|---|
| W160R, A234V, W345R, M374V, T543A | 1140 ± 124 |
| I335T, E483G | 917 ± 200 |
| E233V, V507A | 792 ± 127 |
| W160R, I335T | 366 ± 18 |
| G340S, M487I | 283 ± 36 |
| E233K, F464Y | 146 ± 18 |
| F447S, Q594R | 103 ± 3 |
| wild type | 0 ± 0 |

[a]Transposition frequencies were measured in papillation assay at 25° C. for 140 h on standard papillation medium (LB, Ap 100 µg/ml, Cm 20 µg/ml, Xgal 40 µg/ml, lactose 0.05%, arabinose 1 × 10$^{-4}$%). The number of papillae was enumerated. Papillae number for the wild type MuA protein was 0 ± 0 under these assay conditions. As indicated in FIG. 5, mutations A234V and T543A do not enhance papillation.

REFERENCES

1. Craig N L, Craigie R, Gellert M, Lambowitz A M, editors. (2002) Mobile DNA II. Washington, D.C.: ASM Press. 1204 p.
2. Feschotte C, Pritham E J. (2007) DNA transposons and the evolution of eukaryotic genomes. Annu Rev Genet 41: 331-368.
3. Kazazian H H, Jr. (2004) Mobile elements: Drivers of genome evolution. Science 303: 1626-1632.
4. Muotri A R, Marchetto M C, Coufal N G, Gage F H. (2007) The necessary junk: New functions for transposable elements. Hum Mol Genet 16 Spec No. 2: R159-67.
5. Feschotte C. (2008) Transposable elements and the evolution of regulatory networks. Nat Rev Genet 9: 397-405.
6. Sinzelle L, Izsvak Z, Ivics Z. (2009) Molecular domestication of transposable elements: From detrimental parasites to useful host genes. Cell Mol Life Sci 66: 1073-1093.
7. Boeke J D. (2002) Putting mobile DNA to work: The toolbox. In: Craig N L, Craigie R, Gellert M, Lambowitz A M, editors. Mobile DNA II. Washington, DC: ASM Press. pp. 24-37.
8. Hayes F. (2003) Transposon-based strategies for microbial functional genomics and proteomics. Annu Rev Genet 37: 3-29.
9. Ivics Z, Izsvak Z. (2010) The expanding universe of transposon technologies for gene and cell engineering. Mob DNA 1: 25.
10. Howe M M, Bade E G. (1975) Molecular biology of bacteriophage mu. Science 190: 624-632.
11. Mizuuchi K. (1983) In vitro transposition of bacteriophage Mu: A biochemical approach to a novel replication reaction. Cell 35: 785-794.
12. Mizuuchi K. (1992) Transpositional recombination: Mechanistic insights from studies of Mu and other elements. Annu Rev Biochem 61: 1011-1051.
13. Rice P, Craigie R, Davies D R. (1996) Retroviral integrases and their cousins. Curr Opin Struct Biol 6: 76-83.
14. Nesmelova I V, Hackett P B. (2010) DDE transposases: Structural similarity and diversity. Adv Drug Deliv Rev 62: 1187-1195.
15. Surette M G, Buch S J, Chaconas G. (1987) Transpososomes: Stable protein-DNA complexes involved in the in vitro transposition of bacteriophage Mu DNA. Cell 49: 253-262.

16. Craigie R, Mizuuchi K. (1987) Transposition of mu DNA: Joining of Mu to target DNA can be uncoupled from cleavage at the ends of Mu. Cell 51: 493-501.
17. Baker T A, Mizuuchi M, Savilahti H, Mizuuchi K. (1993) Division of labor among monomers within the Mu transposase tetramer. Cell 74: 723-733.
18. Savilahti H, Rice P A, Mizuuchi K. (1995) The phage Mu transpososome core: DNA requirements for assembly and function. EMBO J 14: 4893-4903.
19. Chaconas G, Harshey R M. (2002) Transposition of phage Mu DNA. In: Craig N L, Craigie R, Gellert M, Lambowitz A M, editors. Mobile DNA II. Washington, D.C.: ASM Press. pp. 384-402.
20. Haapa S, Taira S, Heikkinen E, Savilahti H. (1999) An efficient and accurate integration of mini-Mu transposons in vitro: A general methodology for functional genetic analysis and molecular biology applications. Nucleic Acids Res 27: 2777-2784.
21. Aldaz H, Schuster E, Baker T A. (1996) The interwoven architecture of the Mu transposase couples DNA synapsis to catalysis. Cell 85: 257-269.
22. Savilahti H, Mizuuchi K. (1996) Mu transpositional recombination: Donor DNA cleavage and strand transfer in trans by the Mu transposase. Cell 85: 271-280.
23. Yang J-Y, Jayaram M, Harshey R M. (1996) Positional information within the Mu transposase tetramer: Catalytic contributions of individual monomers. Cell 85: 447-455.
24. Haapa S, Suomalainen S, Eerikainen S, Airaksinen M, Paulin L, et al. (1999) An efficient DNA sequencing strategy based on the bacteriophage Mu in vitro DNA transposition reaction. Genome Res 9: 308-315.
25. Orsini L, Pajunen M, Hanski I, Savilahti H. (2007) SNP discovery by mismatch-targeting of Mu transposition. Nucleic Acids Res 35: e44.
26. Pajunen M, Turakainen H, Poussu E, Peranen J, Vihinen M, et al. (2007) High-precision mapping of protein-protein interfaces: An integrated genetic strategy combining en masse mutagenesis and DNA-level parallel analysis on a yeast two-hybrid platform. Nucleic Acids Res 35: e103.
27. Poussu E, Jantti J, Savilahti H. (2005) A gene truncation strategy generating N- and C-terminal deletion variants of proteins for functional studies: Mapping of the Sec 1p binding domain in yeast Msolp by a Mu in vitro transposition-based approach. Nucleic Acids Res 33: e104.
28. Poussu E, Vihinen M, Paulin L, Savilahti H. (2004) Probing the α-complementing domain of E. coli β-galactosidase with use of an insertional pentapeptide mutagenesis strategy based on Mu in vitro DNA transposition. Proteins 54: 681-692.
29. Brady T, Roth S L, Malani N, Wang G P, Berry C C, et al. (2011) A method to sequence and quantify DNA integration for monitoring outcome in gene therapy. Nucleic Acids Res 39: e72.
30. Krupovič M, Vilen H, Bamford J K H, Kivelä H M, Aalto J-M, et al. (2006) Genome characterization of lipid-containing marine bacteriophage P M2 by transposon insertion mutagenesis. J Virol 80: 9270-9278.
31. Vilen H, Aalto J-M, Kassinen A, Paulin L, Savilahti H. (2003) A direct transposon insertion tool for modification and functional analysis of viral genomes. J Virol 77: 123-134.
32. Lamberg A, Nieminen S, Qiao M, Savilahti H. (2002) Efficient insertion mutagenesis strategy for bacterial genomes involving electroporation of in vitro-assembled DNA transposition complexes of bacteriophage Mu. Appl Environ Microbiol 68: 705-712.
33. Pajunen M I, Pulliainen A T, Finne J, Savilahti H. (2005) Generation of transposon insertion mutant libraries for Gram-positive bacteria by electroporation of phage Mu DNA transposition complexes. Microbiology 151: 1209-1218.
34. Paatero A O, Turakainen H, Happonen L J, Olsson C, Palomaki T, et al. (2008) Bacteriophage Mu integration in yeast and mammalian genomes. Nucleic Acids Res 36: e148.
35. Nakayama C, Teplow D B, Harshey R M. (1987) Structural domains in phage Mu transposase: Identification of the site-specific DNA-binding domain. Proc Natl Acad Sci USA 84: 1809-1813.
36. Clubb R T, Omichinski J G, Savilahti H, Mizuuchi K, Gronenborn A M, et al. (1994) A novel class of winged helix-turn-helix protein: The DNA-binding domain of Mu transposase. Structure 2: 1041-1048.
37. Clubb R T, Schumacher S, Mizuuchi K, Gronenborn A M, Clore G M. (1997) Solution structure of the Iγ subdomain of the Mu end DNA-binding domain of phage Mu transposase. J Mol Biol 273: 19-25.
38. Schumacher S, Clubb R T, Cai M, Mizuuchi K, Clore G M, et al. (1997) Solution structure of the Mu end DNA-binding Iβ subdomain of phage Mu transposase: Modular DNA recognition by two tethered domains. EMBO J 16: 7532-7541.
39. Rice P, Mizuuchi K. (1995) Structure of the bacteriophage Mu transposase core: A common structural motif for DNA transposition and retroviral integration. Cell 82: 209-220.
40. Leung P C, Teplow D B, Harshey R M. (1989) Interaction of distinct domains in Mu transposase with Mu DNA ends and an internal transpositional enhancer. Nature 338: 656-658.
41. Mizuuchi M, Mizuuchi K. (1989) Efficient Mu transposition requires interaction of transposase with a DNA sequence at the Mu operator: Implications for regulation. Cell 58: 399-408.
42. Baker T A, Luo L. (1994) Identification of residues in the Mu transposase essential for catalysis. Proc Natl Acad Sci USA 91: 6654-6658.
43. Krementsova E, Giffin M J, Pincus D, Baker T A. (1998) Mutational analysis of the Mu transposase: Contributions of two distinct regions of domain II to recombination. J Biol Chem 273: 31358-31365.
44. Wu Z, Chaconas G. (1995) A novel DNA binding and nuclease activity in domain III of Mu transposase: Evidence for a catalytic region involved in donor cleavage. EMBO J 14: 3835-3843.
45. Choi W, Harshey R M. (2010) DNA repair by the cryptic endonuclease activity of Mu transposase. Proc Natl Acad Sci USA 107: 10014-10019.
46. Harshey R M, Cuneo S D. (1986) Carboxyl-terminal mutants of phage Mu transposase. J Genet 65: 159-174.
47. Baker T A, Mizuuchi M, Mizuuchi K. (1991) MuB protein allosterically activates strand transfer by the transposase of phage Mu. Cell 65: 1003-1013.
48. Leung P C, Harshey R M. (1991) Two mutations of phage Mu transposase that affect strand transfer or interactions with B protein lie in distinct polypeptide domains. J Mol Biol 219: 189-199.
49. Wu Z, Chaconas G. (1992) Flanking host sequences can exert an inhibitory effect on the cleavage step of the in vitro Mu DNA strand transfer reaction. J Biol Chem 267: 9552-9558.
50. Levchenko I, Luo L, Baker T A. (1995) Disassembly of the Mu transposase tetramer by the ClpX chaperone. Genes Dev 9: 2399-2408.

51. Pajunen M I, Rasila T S, Happonen L J, Lamberg A, Haapa-Paananen S, et al. (2010) Universal platform for quantitative analysis of DNA transposition. Mob DNA 1: 24.
52. Kim Y C, Morrison S L. (2009) N-terminal domain-deleted Mu transposase exhibits increased transposition activity with low target site preference in modified buffers. J Mol Microbiol Biotechnol 17: 30-40.
53. Rasila T S, Pajunen M I, Savilahti H. (2009) Critical evaluation of random mutagenesis by error-prone polymerase chain reaction protocols, *Escherichia coli* mutator strain, and hydroxylamine treatment. Anal Biochem 388: 71-80.
54. Grant S G, Jessee J, Bloom F R, Hanahan D. (1990) Differential plasmid rescue from transgenic mouse DNAs into *Escherichia coli* methylation-restriction mutants. Proc Natl Acad Sci USA 87: 4645-4649.
55. Meissner P S, Sisk W P, Berman M L. (1987) Bacteriophage lambda cloning system for the construction of directional cDNA libraries. Proc Natl Acad Sci USA 84: 4171-4175.
56. Sambrook J, Russell DW. (2001) Molecular cloning: A laboratory manual. Cold Spring Harbor, N.Y.: Cold Spring Harbor Laboratory Press. 2344 p.
57. Hanahan D, Jessee J, Bloom F R. (1991) Plasmid transformation of *Escherichia coli* and other bacteria. Methods Enzymol 204: 63-113.
58. Bradford M M. (1976) A rapid and sensitive method for the quantitation of microgram quantities of protein utilizing the principle of protein-dye binding. Anal Biochem 72: 248-254.
59. Reznikoff W S. (2003) Tn5 as a model for understanding DNA transposition. Mol Microbiol 47: 1199-1206.
60. Mates L, Chuah M K, Belay E, Jerchow B, Manoj N, et al. (2009) Molecular evolution of a novel hyperactive Sleeping Beauty transposase enables robust stable gene transfer in vertebrates. Nat Genet 41: 753-761.
61. Germon S, Bouchet N, Casteret S, Carpentier G, Adet J, et al. (2009) *Mariner* Mos1 transposase optimization by rational mutagenesis. Genetica 137: 265-276.
62. Beall E L, Mahoney M B, Rio DC. (2002) Identification and analysis of a hyperactive mutant form of *Drosophila* P-element transposase. Genetics 162: 217-227.

---

The invention claimed is:

1. A method for producing a hyperactive MuA transposase variant comprising at least one single-amino-acid-change, the method comprising the steps of
modifying the nucleic acid encoding wild type MuA transposase so that the modified nucleic acid encodes a MuA transposase variant comprising at least one single-amino-acid change at the amino acid positions of SEQ ID NO: 1 selected from the group consisting of:
A59V, D97G, W160R, E179V, E233K, E233V, Q254R, E258G, G302D, I335T, G340S, W345C, W345R, M374V, F447S, F464Y, R478H, R478C, E482K, E483G, E483V, M487I, V495A, V507A, Q539H, Q539R, and I617T; and
producing a MuA transposase variant by expressing the modified nucleic acid in a host cell and identifying those MuA variants the transposase activity of which is higher than the transposase activity of the wild type MuA.

2. A method for producing a hyperactive MuA transposase variant comprising at least one single-amino-acid-change, the method comprising the steps of
modifying the nucleic acid encoding wild type MuA transposase so that the modified nucleic acid encodes a MuA transposase variant comprising at least one single-amino-acid change at the amino acid positions of SEQ ID NO: 1; and
producing a MuA transposase variant by expressing the modified nucleic acid in a host cell and identifying those MuA variants the transposase activity of which is higher than the transposase activity of the wild type MuA,
wherein said MuA transposase variant has the single-amino-acid-change at position 233.

3. The method according to claim 2, wherein the MuA transposase variant produced has the following single-amino-acid-changes: W160R, E233K, and W345R.

4. A hyperactive MuA transposase comprising at least one of the single-amino-acid-changes selected from the group consisting of:
A59V, D97G, W160R, E179V, E233K, E233V, Q254R, E258G, G302D, I335T, G340S, W345C, W345R, M374V, F447S, F464Y, R478H, R478C, E482K, E483G, E483V, M487I, V495A, V507A, Q539H, Q539R, and I617T.

5. The hyperactive MuA transposase according to claim 4 comprising two or three of said single-amino-acid-changes.

6. A hyperactive MuA transposase comprising a single-amino-acid-change at position 233 of SEQ ID NO: 1.

7. The hyperactive MuA transposase according to claim 6 comprising or consisting of the amino acid sequence as set forth in SEQ ID NO: 2 with the single-amino-acid-change E233V.

8. The hyperactive MuA transposase according to claim 6 comprising the following single-amino-acid-changes: W160R, E233K, and W345R.

9. The hyperactive MuA transposase according to claim 6 comprising or consisting of the amino acid sequence as set forth in SEQ ID NO: 3.

10. A kit for performing a transposase reaction comprising the hyperactive MuA transposase according to claim 4.

11. The kit according to claim 10, wherein said kit comprises means for DNA sequencing.

12. A kit for performing a transposase reaction comprising the hyperactive MuA transposase according to claim 6.

13. The kit according to claim 12, wherein said kit comprises means for DNA sequencing.

14. A method for producing a hyperactive MuA transposase variant, the method consisting of the steps of
modifying the nucleic acid encoding wild type MuA transposase so that the modified nucleic acid encodes a MuA transposase variant with a single-amino-acid change or single-amino-acid changes at the amino acid positions of SEQ ID NO: 1 selected from the group consisting of: 59, 97, 160, 179, 233, 254, 258, 302, 335, 340, 345, 374, 447, 464, 478, 482, 483, 487, 495, 507, 539, 594, and 617;
producing a MuA transposase variant by expressing the modified nucleic acid in a host cell; and
identifying those MuA variants the transposase activity of which is higher than the transposase activity of the wild type MuA.

* * * * *

SEQUENCE LISTING

```
<160> NUMBER OF SEQ ID NOS: 86

<210> SEQ ID NO 1
<211> LENGTH: 663
<212> TYPE: PRT
<213> ORGANISM: Mu phage

<400> SEQUENCE: 1

Met Glu Leu Trp Val Ser Pro Lys Glu Cys Ala Asn Leu Pro Gly Leu
1               5                   10                  15

Pro Lys Thr Ser Ala Gly Val Ile Tyr Val Ala Lys Lys Gln Gly Trp
            20                  25                  30

Gln Asn Arg Thr Arg Ala Gly Val Lys Gly Lys Ala Ile Glu Tyr
        35                  40                  45

Asn Ala Asn Ser Leu Pro Val Glu Ala Lys Ala Ala Leu Leu Leu Arg
    50                  55                  60

Gln Gly Glu Ile Glu Thr Ser Leu Gly Tyr Phe Glu Ile Ala Arg Pro
65                  70                  75                  80

Thr Leu Glu Ala His Asp Tyr Asp Arg Glu Ala Leu Trp Ser Lys Trp
                85                  90                  95

Asp Asn Ala Ser Asp Ser Gln Arg Arg Leu Ala Glu Lys Trp Leu Pro
            100                 105                 110

Ala Val Gln Ala Ala Asp Glu Met Leu Asn Gln Gly Ile Ser Thr Lys
        115                 120                 125

Thr Ala Phe Ala Thr Val Ala Gly His Tyr Gln Val Ser Ala Ser Thr
    130                 135                 140

Leu Arg Asp Lys Tyr Tyr Gln Val Gln Lys Phe Ala Lys Pro Asp Trp
145                 150                 155                 160

Ala Ala Ala Leu Val Asp Gly Arg Gly Ala Ser Arg Asn Val His
                165                 170                 175

Lys Ser Glu Phe Asp Glu Asp Ala Trp Gln Phe Leu Ile Ala Asp Tyr
            180                 185                 190

Leu Arg Pro Glu Lys Pro Ala Phe Arg Lys Cys Tyr Glu Arg Leu Glu
        195                 200                 205

Leu Ala Ala Arg Glu His Gly Trp Ser Ile Pro Ser Arg Ala Thr Ala
    210                 215                 220
```

-continued

```
Phe Arg Arg Ile Gln Gln Leu Asp Glu Ala Met Val Ala Cys Arg
225                 230                 235                 240

Glu Gly Glu His Ala Leu Met His Leu Ile Pro Ala Gln Gln Arg Thr
            245                 250                 255

Val Glu His Leu Asp Ala Met Gln Trp Ile Asn Gly Asp Gly Tyr Leu
        260                 265                 270

His Asn Val Phe Val Arg Trp Phe Asn Gly Asp Val Ile Arg Pro Lys
            275                 280                 285

Thr Trp Phe Trp Gln Asp Val Lys Thr Arg Lys Ile Leu Gly Trp Arg
    290                 295                 300

Cys Asp Val Ser Glu Asn Ile Asp Ser Ile Arg Leu Ser Phe Met Asp
305                 310                 315                 320

Val Val Thr Arg Tyr Gly Ile Pro Glu Asp Phe His Ile Thr Ile Asp
                325                 330                 335

Asn Thr Arg Gly Ala Ala Asn Lys Trp Leu Thr Gly Gly Ala Pro Asn
            340                 345                 350

Arg Tyr Arg Phe Lys Val Lys Glu Asp Pro Lys Gly Leu Phe Leu
        355                 360                 365

Leu Met Gly Ala Lys Met His Trp Thr Ser Val Ala Gly Lys Gly
370                 375                 380

Trp Gly Gln Ala Lys Pro Val Glu Arg Ala Phe Gly Val Gly Leu
385                 390                 395                 400

Glu Glu Tyr Val Asp Lys His Pro Ala Leu Ala Gly Ala Tyr Thr Gly
                405                 410                 415

Pro Asn Pro Gln Ala Lys Pro Asp Asn Tyr Gly Asp Arg Ala Val Asp
            420                 425                 430

Ala Glu Leu Phe Leu Lys Thr Leu Ala Glu Gly Val Ala Met Phe Asn
        435                 440                 445

Ala Arg Thr Gly Arg Glu Thr Glu Met Cys Gly Gly Lys Leu Ser Phe
    450                 455                 460

Asp Asp Val Phe Glu Arg Glu Tyr Ala Arg Thr Ile Val Arg Lys Pro
465                 470                 475                 480

Thr Glu Glu Gln Lys Arg Met Leu Leu Leu Pro Ala Glu Ala Val Asn
                485                 490                 495

Val Ser Arg Lys Gly Glu Phe Thr Leu Lys Val Gly Gly Ser Leu Lys
            500                 505                 510

Gly Ala Lys Asn Val Tyr Tyr Asn Met Ala Leu Met Asn Ala Gly Val
        515                 520                 525

Lys Lys Val Val Val Arg Phe Asp Pro Gln Gln Leu His Ser Thr Val
    530                 535                 540

Tyr Cys Tyr Thr Leu Asp Gly Arg Phe Ile Cys Glu Ala Glu Cys Leu
545                 550                 555                 560

Ala Pro Val Ala Phe Asn Asp Ala Ala Ala Gly Arg Glu Tyr Arg Arg
                565                 570                 575

Arg Gln Lys Gln Leu Lys Ser Ala Thr Lys Ala Ala Ile Lys Ala Gln
            580                 585                 590

Lys Gln Met Asp Ala Leu Glu Val Ala Glu Leu Leu Pro Gln Ile Ala
        595                 600                 605

Glu Pro Ala Ala Pro Glu Ser Arg Ile Val Gly Ile Phe Arg Pro Ser
    610                 615                 620

Gly Asn Thr Glu Arg Val Lys Asn Gln Glu Arg Asp Asp Glu Tyr Glu
625                 630                 635                 640
```

Thr Glu Arg Asp Glu Tyr Leu Asn His Ser Leu Asp Ile Leu Glu Gln
                645                 650                 655

Asn Arg Arg Lys Lys Ala Ile
            660

<210> SEQ ID NO 2
<211> LENGTH: 663
<212> TYPE: PRT
<213> ORGANISM: Artificial sequence
<220> FEATURE:
<223> OTHER INFORMATION: Recombinant MuA variant

<400> SEQUENCE: 2

Met Glu Leu Trp Val Ser Pro Lys Glu Cys Ala Asn Leu Pro Gly Leu
1               5                   10                  15

Pro Lys Thr Ser Ala Gly Val Ile Tyr Val Ala Lys Lys Gln Gly Trp
            20                  25                  30

Gln Asn Arg Thr Arg Ala Gly Val Lys Gly Gly Lys Ala Ile Glu Tyr
        35                  40                  45

Asn Ala Asn Ser Leu Pro Val Glu Ala Lys Ala Ala Leu Leu Leu Arg
    50                  55                  60

Gln Gly Glu Ile Glu Thr Ser Leu Gly Tyr Phe Glu Ile Ala Arg Pro
65                  70                  75                  80

Thr Leu Glu Ala His Asp Tyr Asp Arg Glu Ala Leu Trp Ser Lys Trp
                85                  90                  95

Asp Asn Ala Ser Asp Ser Gln Arg Arg Leu Ala Glu Lys Trp Leu Pro
            100                 105                 110

Ala Val Gln Ala Ala Asp Glu Met Leu Asn Gln Gly Ile Ser Thr Lys
        115                 120                 125

Thr Ala Phe Ala Thr Val Ala Gly His Tyr Gln Val Ser Ala Ser Thr
    130                 135                 140

Leu Arg Asp Lys Tyr Tyr Gln Val Gln Lys Phe Ala Lys Pro Asp Trp
145                 150                 155                 160

Ala Ala Ala Leu Val Asp Gly Arg Gly Ala Ser Arg Arg Asn Val His
                165                 170                 175

Lys Ser Glu Phe Asp Glu Asp Ala Trp Gln Phe Leu Ile Ala Asp Tyr
            180                 185                 190

Leu Arg Pro Glu Lys Pro Ala Phe Arg Lys Cys Tyr Glu Arg Leu Glu
        195                 200                 205

Leu Ala Ala Arg Glu His Gly Trp Ser Ile Pro Ser Arg Ala Thr Ala
    210                 215                 220

Phe Arg Arg Ile Gln Gln Leu Asp Val Ala Met Val Val Ala Cys Arg
225                 230                 235                 240

Glu Gly Glu His Ala Leu Met His Leu Ile Pro Ala Gln Gln Arg Thr
                245                 250                 255

Val Glu His Leu Asp Ala Met Gln Trp Ile Asn Gly Asp Gly Tyr Leu
            260                 265                 270

His Asn Val Phe Val Arg Trp Phe Asn Gly Asp Val Ile Arg Pro Lys
        275                 280                 285

Thr Trp Phe Trp Gln Asp Val Lys Thr Arg Lys Ile Leu Gly Trp Arg
    290                 295                 300

Cys Asp Val Ser Glu Asn Ile Asp Ser Ile Arg Leu Ser Phe Met Asp
305                 310                 315                 320

Val Val Thr Arg Tyr Gly Ile Pro Glu Asp Phe His Ile Thr Ile Asp
                325                 330                 335

```
Asn Thr Arg Gly Ala Ala Asn Lys Trp Leu Thr Gly Gly Ala Pro Asn
                340                 345                 350
Arg Tyr Arg Phe Lys Val Lys Glu Asp Asp Pro Lys Gly Leu Phe Leu
            355                 360                 365
Leu Met Gly Ala Lys Met His Trp Thr Ser Val Val Ala Gly Lys Gly
        370                 375                 380
Trp Gly Gln Ala Lys Pro Val Glu Arg Ala Phe Gly Val Gly Gly Leu
385                 390                 395                 400
Glu Glu Tyr Val Asp Lys His Pro Ala Leu Ala Gly Ala Tyr Thr Gly
                405                 410                 415
Pro Asn Pro Gln Ala Lys Pro Asp Asn Tyr Gly Asp Arg Ala Val Asp
            420                 425                 430
Ala Glu Leu Phe Leu Lys Thr Leu Ala Glu Gly Val Ala Met Phe Asn
        435                 440                 445
Ala Arg Thr Gly Arg Glu Thr Glu Met Cys Gly Gly Lys Leu Ser Phe
    450                 455                 460
Asp Asp Val Phe Glu Arg Glu Tyr Ala Arg Thr Ile Val Arg Lys Pro
465                 470                 475                 480
Thr Glu Glu Gln Lys Arg Met Leu Leu Leu Pro Ala Glu Ala Val Asn
                485                 490                 495
Val Ser Arg Lys Gly Glu Phe Thr Leu Lys Val Gly Gly Ser Leu Lys
            500                 505                 510
Gly Ala Lys Asn Val Tyr Tyr Asn Met Ala Leu Met Asn Ala Gly Val
        515                 520                 525
Lys Lys Val Val Arg Phe Asp Pro Gln Gln Leu His Ser Thr Val
    530                 535                 540
Tyr Cys Tyr Thr Leu Asp Gly Arg Phe Ile Cys Glu Ala Glu Cys Leu
545                 550                 555                 560
Ala Pro Val Ala Phe Asn Asp Ala Ala Gly Arg Glu Tyr Arg Arg
                565                 570                 575
Arg Gln Lys Gln Leu Lys Ser Ala Thr Lys Ala Ala Ile Lys Ala Gln
            580                 585                 590
Lys Gln Met Asp Ala Leu Glu Val Ala Glu Leu Leu Pro Gln Ile Ala
        595                 600                 605
Glu Pro Ala Ala Pro Glu Ser Arg Ile Val Gly Ile Phe Arg Pro Ser
    610                 615                 620
Gly Asn Thr Glu Arg Val Lys Asn Gln Glu Arg Asp Asp Glu Tyr Glu
625                 630                 635                 640
Thr Glu Arg Asp Glu Tyr Leu Asn His Ser Leu Asp Ile Leu Glu Gln
                645                 650                 655
Asn Arg Arg Lys Lys Ala Ile
            660

<210> SEQ ID NO 3
<211> LENGTH: 663
<212> TYPE: PRT
<213> ORGANISM: Artificial sequence
<220> FEATURE:
<223> OTHER INFORMATION: Recombinant MuA variant

<400> SEQUENCE: 3

Met Glu Leu Trp Val Ser Pro Lys Glu Cys Ala Asn Leu Pro Gly Leu
1               5                   10                  15
Pro Lys Thr Ser Ala Gly Val Ile Tyr Val Ala Lys Lys Gln Gly Trp
            20                  25                  30
```

```
Gln Asn Arg Thr Arg Ala Gly Val Lys Gly Lys Ala Ile Glu Tyr
         35                  40                  45

Asn Ala Asn Ser Leu Pro Val Glu Ala Lys Ala Leu Leu Leu Arg
 50                  55                  60

Gln Gly Glu Ile Glu Thr Ser Leu Gly Tyr Phe Glu Ile Ala Arg Pro
 65                  70                  75                  80

Thr Leu Glu Ala His Asp Tyr Asp Arg Glu Ala Leu Trp Ser Lys Trp
                 85                  90                  95

Asp Asn Ala Ser Asp Ser Gln Arg Arg Leu Ala Glu Lys Trp Leu Pro
                100                 105                 110

Ala Val Gln Ala Ala Asp Glu Met Leu Asn Gln Gly Ile Ser Thr Lys
                115                 120                 125

Thr Ala Phe Ala Thr Val Ala Gly His Tyr Gln Val Ser Ala Ser Thr
    130                 135                 140

Leu Arg Asp Lys Tyr Tyr Gln Val Gln Lys Phe Ala Lys Pro Asp Arg
145                 150                 155                 160

Ala Ala Ala Leu Val Asp Gly Arg Gly Ala Ser Arg Arg Asn Val His
                165                 170                 175

Lys Ser Glu Phe Asp Glu Asp Ala Trp Gln Phe Leu Ile Ala Asp Tyr
                180                 185                 190

Leu Arg Pro Glu Lys Pro Ala Phe Arg Lys Cys Tyr Glu Arg Leu Glu
                195                 200                 205

Leu Ala Ala Arg Glu His Gly Trp Ser Ile Pro Ser Arg Ala Thr Ala
                210                 215                 220

Phe Arg Arg Ile Gln Gln Leu Asp Lys Ala Met Val Ala Cys Arg
225                 230                 235                 240

Glu Gly Glu His Ala Leu Met His Leu Ile Pro Ala Gln Gln Arg Thr
                245                 250                 255

Val Glu His Leu Asp Ala Met Gln Trp Ile Asn Gly Asp Gly Tyr Leu
                260                 265                 270

His Asn Val Phe Val Arg Trp Phe Asn Gly Asp Val Ile Arg Pro Lys
                275                 280                 285

Thr Trp Phe Trp Gln Asp Val Lys Thr Arg Lys Ile Leu Gly Trp Arg
    290                 295                 300

Cys Asp Val Ser Glu Asn Ile Asp Ser Ile Arg Leu Ser Phe Met Asp
305                 310                 315                 320

Val Val Thr Arg Tyr Gly Ile Pro Glu Asp Phe His Ile Thr Ile Asp
                325                 330                 335

Asn Thr Arg Gly Ala Ala Asn Lys Arg Leu Thr Gly Ala Pro Asn
                340                 345                 350

Arg Tyr Arg Phe Lys Val Lys Glu Asp Asp Pro Lys Gly Leu Phe Leu
                355                 360                 365

Leu Met Gly Ala Lys Met His Trp Thr Ser Val Val Ala Gly Lys Gly
    370                 375                 380

Trp Gly Gln Ala Lys Pro Val Arg Ala Phe Gly Val Gly Leu
385                 390                 395                 400

Glu Glu Tyr Val Asp Lys His Pro Ala Leu Ala Gly Ala Tyr Thr Gly
                405                 410                 415

Pro Asn Pro Gln Ala Lys Pro Asp Asn Tyr Gly Asp Arg Ala Val Asp
                420                 425                 430

Ala Glu Leu Phe Leu Lys Thr Leu Ala Glu Gly Val Ala Met Phe Asn
    435                 440                 445

Ala Arg Thr Gly Arg Glu Thr Glu Met Cys Gly Gly Lys Leu Ser Phe
```

```
            450                 455                 460
Asp Asp Val Phe Glu Arg Glu Tyr Ala Arg Thr Ile Val Arg Lys Pro
465                 470                 475                 480

Thr Glu Glu Gln Lys Arg Met Leu Leu Leu Pro Ala Glu Ala Val Asn
                485                 490                 495

Val Ser Arg Lys Gly Glu Phe Thr Leu Lys Val Gly Gly Ser Leu Lys
                500                 505                 510

Gly Ala Lys Asn Val Tyr Tyr Asn Met Ala Leu Met Asn Ala Gly Val
                515                 520                 525

Lys Lys Val Val Val Arg Phe Asp Pro Gln Gln Leu His Ser Thr Val
                530                 535                 540

Tyr Cys Tyr Thr Leu Asp Gly Arg Phe Ile Cys Glu Ala Glu Cys Leu
545                 550                 555                 560

Ala Pro Val Ala Phe Asn Asp Ala Ala Gly Arg Glu Tyr Arg Arg
                565                 570                 575

Arg Gln Lys Gln Leu Lys Ser Ala Thr Lys Ala Ala Ile Lys Ala Gln
                580                 585                 590

Lys Gln Met Asp Ala Leu Glu Val Ala Glu Leu Leu Pro Gln Ile Ala
                595                 600                 605

Glu Pro Ala Ala Pro Glu Ser Arg Ile Val Gly Ile Phe Arg Pro Ser
                610                 615                 620

Gly Asn Thr Glu Arg Val Lys Asn Gln Glu Arg Asp Asp Glu Tyr Glu
625                 630                 635                 640

Thr Glu Arg Asp Glu Tyr Leu Asn His Ser Leu Asp Ile Leu Glu Gln
                645                 650                 655

Asn Arg Arg Lys Lys Ala Ile
                660

<210> SEQ ID NO 4
<211> LENGTH: 15
<212> TYPE: DNA
<213> ORGANISM: Artificial sequence
<220> FEATURE:
<223> OTHER INFORMATION: Oligonucleotide primer

<400> SEQUENCE: 4
gatcgccggt accat                                                        15

<210> SEQ ID NO 5
<211> LENGTH: 15
<212> TYPE: DNA
<213> ORGANISM: Artificial sequence
<220> FEATURE:
<223> OTHER INFORMATION: Oligonucleotide primer

<400> SEQUENCE: 5
gatcatggta ccggc                                                        15

<210> SEQ ID NO 6
<211> LENGTH: 16
<212> TYPE: DNA
<213> ORGANISM: Artificial sequence
<220> FEATURE:
<223> OTHER INFORMATION: Oligonucleotide primer

<400> SEQUENCE: 6
agggcggctg cacttg                                                       16

<210> SEQ ID NO 7
```

<211> LENGTH: 19
<212> TYPE: DNA
<213> ORGANISM: Artificial sequence
<220> FEATURE:
<223> OTHER INFORMATION: Oligonucleotide primer

<400> SEQUENCE: 7
gtcaggcttc gcaaacttc                                             19

<210> SEQ ID NO 8
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 8
taatggttgt tgcctgtcgt g                                          21

<210> SEQ ID NO 9
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 9
cctcgtccag ttgctgaatc                                            20

<210> SEQ ID NO 10
<211> LENGTH: 16
<212> TYPE: DNA
<213> ORGANISM: Artificial sequence
<220> FEATURE:
<223> OTHER INFORMATION: Oligonucleotide primer

<400> SEQUENCE: 10
aggctgacgg gaggcg                                                16

<210> SEQ ID NO 11
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 11
tttattcgca gcaccacggg                                            20

<210> SEQ ID NO 12
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 12
gcggtttatt gctacaccct g                                          21

<210> SEQ ID NO 13
<211> LENGTH: 17
<212> TYPE: DNA
<213> ORGANISM: Artificial sequence
<220> FEATURE:
<223> OTHER INFORMATION: Oligonucleotide primer

<400> SEQUENCE: 13

```
gctgtgtagc tgctgcg                                                    17

<210> SEQ ID NO 14
<211> LENGTH: 18
<212> TYPE: DNA
<213> ORGANISM: Artificial sequence
<220> FEATURE:
<223> OTHER INFORMATION: Oligonucleotide primer

<400> SEQUENCE: 14
gtaacgccag cgattccc                                                   18

<210> SEQ ID NO 15
<211> LENGTH: 19
<212> TYPE: DNA
<213> ORGANISM: Artificial sequence
<220> FEATURE:
<223> OTHER INFORMATION: Oligonucleotide primer

<400> SEQUENCE: 15
cccatttgct ccacagtgc                                                  19

<210> SEQ ID NO 16
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 16
tggcaatggt tgttgcctgt c                                               21

<210> SEQ ID NO 17
<211> LENGTH: 19
<212> TYPE: DNA
<213> ORGANISM: Artificial sequence
<220> FEATURE:
<223> OTHER INFORMATION: Oligonucleotide primer

<400> SEQUENCE: 17
cgtccagttg ctgaatccg                                                  19

<210> SEQ ID NO 18
<211> LENGTH: 23
<212> TYPE: DNA
<213> ORGANISM: Artificial sequence
<220> FEATURE:
<223> OTHER INFORMATION: Oligonucleotide primer

<400> SEQUENCE: 18
ttgttgtgac tcgctacggt atc                                             23

<210> SEQ ID NO 19
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 19
ccatgaacga gaggcgaatt g                                               21

<210> SEQ ID NO 20
<211> LENGTH: 18
<212> TYPE: DNA
```

<213> ORGANISM: Artificial sequence
<220> FEATURE:
<223> OTHER INFORMATION: Oligonucleotide primer

<400> SEQUENCE: 20
gctcgctacg gtatcccg                                             18

<210> SEQ ID NO 21
<211> LENGTH: 22
<212> TYPE: DNA
<213> ORGANISM: Artificial sequence
<220> FEATURE:
<223> OTHER INFORMATION: Oligonucleotide primer

<400> SEQUENCE: 21
cacaacatcc atgaacgaga gg                                        22

<210> SEQ ID NO 22
<211> LENGTH: 19
<212> TYPE: DNA
<213> ORGANISM: Artificial sequence
<220> FEATURE:
<223> OTHER INFORMATION: Oligonucleotide primer

<400> SEQUENCE: 22
agtgctgcga ataaatggc                                            19

<210> SEQ ID NO 23
<211> LENGTH: 22
<212> TYPE: DNA
<213> ORGANISM: Artificial sequence
<220> FEATURE:
<223> OTHER INFORMATION: Oligonucleotide primer

<400> SEQUENCE: 23
acgggtgtta tcaatggtga tg                                        22

<210> SEQ ID NO 24
<211> LENGTH: 16
<212> TYPE: DNA
<213> ORGANISM: Artificial sequence
<220> FEATURE:
<223> OTHER INFORMATION: Oligonucleotide primer

<400> SEQUENCE: 24
cctgacggga ggcgcg                                               16

<210> SEQ ID NO 25
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 25
catttattcg cagcaccacg g                                         21

<210> SEQ ID NO 26
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 26
atgatgatgt tttcgagcgt g                                         21

<210> SEQ ID NO 27
<211> LENGTH: 17
<212> TYPE: DNA
<213> ORGANISM: Artificial sequence
<220> FEATURE:
<223> OTHER INFORMATION: Oligonucleotide primer

<400> SEQUENCE: 27
acgagagttt gcccccg                                                17

<210> SEQ ID NO 28
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 28
gtgttttcga gcgtgaatac g                                           21

<210> SEQ ID NO 29
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 29
catcaaacga gagtttgccc c                                           21

<210> SEQ ID NO 30
<211> LENGTH: 23
<212> TYPE: DNA
<213> ORGANISM: Artificial sequence
<220> FEATURE:
<223> OTHER INFORMATION: Oligonucleotide primer

<400> SEQUENCE: 30
gacaaaaacg gatgctgtta ctg                                         23

<210> SEQ ID NO 31
<211> LENGTH: 19
<212> TYPE: DNA
<213> ORGANISM: Artificial sequence
<220> FEATURE:
<223> OTHER INFORMATION: Oligonucleotide primer

<400> SEQUENCE: 31
cttcggttgg cttacgcac                                              19

<210> SEQ ID NO 32
<211> LENGTH: 19
<212> TYPE: DNA
<213> ORGANISM: Artificial sequence
<220> FEATURE:
<223> OTHER INFORMATION: Oligonucleotide primer

<400> SEQUENCE: 32
actgttactg cctgccgag                                              19

<210> SEQ ID NO 33
<211> LENGTH: 23
<212> TYPE: DNA
<213> ORGANISM: Artificial sequence
<220> FEATURE:

<223> OTHER INFORMATION: Oligonucleotide primer

<400> SEQUENCE: 33
atccgttttt gttcttcggt tgg                                               23

<210> SEQ ID NO 34
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 34
cgaacgtttc acgcaaaggc                                                   20

<210> SEQ ID NO 35
<211> LENGTH: 16
<212> TYPE: DNA
<213> ORGANISM: Artificial sequence
<220> FEATURE:
<223> OTHER INFORMATION: Oligonucleotide primer

<400> SEQUENCE: 35
ccgcctcggc aggcag                                                       16

<210> SEQ ID NO 36
<211> LENGTH: 19
<212> TYPE: DNA
<213> ORGANISM: Artificial sequence
<220> FEATURE:
<223> OTHER INFORMATION: Oligonucleotide primer

<400> SEQUENCE: 36
ctggcggctc ccttaaagg                                                    19

<210> SEQ ID NO 37
<211> LENGTH: 23
<212> TYPE: DNA
<213> ORGANISM: Artificial sequence
<220> FEATURE:
<223> OTHER INFORMATION: Oligonucleotide primer

<400> SEQUENCE: 37
ctttaagcgt aaactcgcct ttg                                               23

<210> SEQ ID NO 38
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 38
gaatggacgc gctggaagtt g                                                 21

<210> SEQ ID NO 39
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 39
gtttctgcgc cttaatggct g                                                 21

```
<210> SEQ ID NO 40
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 40
tggcgttatt gctgagacaa g                                              21

<210> SEQ ID NO 41
<211> LENGTH: 23
<212> TYPE: DNA
<213> ORGANISM: Artificial sequence
<220> FEATURE:
<223> OTHER INFORMATION: Oligonucleotide primer

<400> SEQUENCE: 41
ctttcgcttc aacaggtaaa gag                                            23

<210> SEQ ID NO 42
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 42
acttttgcga ccgttgcagg                                                20

<210> SEQ ID NO 43
<211> LENGTH: 22
<212> TYPE: DNA
<213> ORGANISM: Artificial sequence
<220> FEATURE:
<223> OTHER INFORMATION: Oligonucleotide primer

<400> SEQUENCE: 43
cgttttcgtt gaaatcccct gg                                             22

<210> SEQ ID NO 44
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 44
catttgacga ggatgcctgg                                                20

<210> SEQ ID NO 45
<211> LENGTH: 22
<212> TYPE: DNA
<213> ORGANISM: Artificial sequence
<220> FEATURE:
<223> OTHER INFORMATION: Oligonucleotide primer

<400> SEQUENCE: 45
cacttttgtg aacattgcga cg                                             22

<210> SEQ ID NO 46
<211> LENGTH: 21
<212> TYPE: DNA
<213> ORGANISM: Artificial sequence
<220> FEATURE:
<223> OTHER INFORMATION: Oligonucleotide primer
```

```
<400> SEQUENCE: 46
tatttgacga ggatgcctgg c                                              21

<210> SEQ ID NO 47
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 47
ggcgaactgt ggaacacctg g                                              21

<210> SEQ ID NO 48
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 48
gctgtgccgg tatcagatgc                                                20

<210> SEQ ID NO 49
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 49
aaagaacaaa aacggatgct g                                              21

<210> SEQ ID NO 50
<211> LENGTH: 19
<212> TYPE: DNA
<213> ORGANISM: Artificial sequence
<220> FEATURE:
<223> OTHER INFORMATION: Oligonucleotide primer

<400> SEQUENCE: 50
ggttggctta cgcacaatc                                                 19

<210> SEQ ID NO 51
<211> LENGTH: 24
<212> TYPE: DNA
<213> ORGANISM: Artificial sequence
<220> FEATURE:
<223> OTHER INFORMATION: Oligonucleotide primer

<400> SEQUENCE: 51
tacaaaaacg gatgctgtta ctgc                                           24

<210> SEQ ID NO 52
<211> LENGTH: 22
<212> TYPE: DNA
<213> ORGANISM: Artificial sequence
<220> FEATURE:
<223> OTHER INFORMATION: Oligonucleotide primer

<400> SEQUENCE: 52
tctacacagc acggtttatt gc                                             22

<210> SEQ ID NO 53
<211> LENGTH: 20
```

```
<212> TYPE: DNA
<213> ORGANISM: Artificial sequence
<220> FEATURE:
<223> OTHER INFORMATION: Oligonucleotide primer

<400> SEQUENCE: 53
tgctgcggat caaacctgac                                           20

<210> SEQ ID NO 54
<211> LENGTH: 22
<212> TYPE: DNA
<213> ORGANISM: Artificial sequence
<220> FEATURE:
<223> OTHER INFORMATION: Oligonucleotide primer

<400> SEQUENCE: 54
ggctacacag cacggtttat tg                                        22

<210> SEQ ID NO 55
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 55
gctgcggatc aaacctgacc                                           20

<210> SEQ ID NO 56
<211> LENGTH: 22
<212> TYPE: DNA
<213> ORGANISM: Artificial sequence
<220> FEATURE:
<223> OTHER INFORMATION: Oligonucleotide primer

<400> SEQUENCE: 56
ctgttggtat tttccggcct tc                                        22

<210> SEQ ID NO 57
<211> LENGTH: 19
<212> TYPE: DNA
<213> ORGANISM: Artificial sequence
<220> FEATURE:
<223> OTHER INFORMATION: Oligonucleotide primer

<400> SEQUENCE: 57
ttcgtgattc tggtgctgc                                            19

<210> SEQ ID NO 58
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 58
cgaatcattc gctggatatt c                                         21

<210> SEQ ID NO 59
<211> LENGTH: 22
<212> TYPE: DNA
<213> ORGANISM: Artificial sequence
<220> FEATURE:
<223> OTHER INFORMATION: Oligonucleotide primer

<400> SEQUENCE: 59
```

```
gatattcatc acgctcagtt tc                                            22

<210> SEQ ID NO 60
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 60
agaatcattc gctggatatt c                                             21

<210> SEQ ID NO 61
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 61
acgctggata ttctggaaca g                                             21

<210> SEQ ID NO 62
<211> LENGTH: 24
<212> TYPE: DNA
<213> ORGANISM: Artificial sequence
<220> FEATURE:
<223> OTHER INFORMATION: Oligonucleotide primer

<400> SEQUENCE: 62
atgattcaga tattcatcac gctc                                          24

<210> SEQ ID NO 63
<211> LENGTH: 23
<212> TYPE: DNA
<213> ORGANISM: Artificial sequence
<220> FEATURE:
<223> OTHER INFORMATION: Oligonucleotide primer

<400> SEQUENCE: 63
atggatattc tggaacagaa cag                                           23

<210> SEQ ID NO 64
<211> LENGTH: 24
<212> TYPE: DNA
<213> ORGANISM: Artificial sequence
<220> FEATURE:
<223> OTHER INFORMATION: Oligonucleotide primer

<400> SEQUENCE: 64
cgaatgattc agatattcat cacg                                          24

<210> SEQ ID NO 65
<211> LENGTH: 22
<212> TYPE: DNA
<213> ORGANISM: Artificial sequence
<220> FEATURE:
<223> OTHER INFORMATION: Oligonucleotide primer

<400> SEQUENCE: 65
cggatattct ggaacagaac ag                                            22

<210> SEQ ID NO 66
<211> LENGTH: 24
<212> TYPE: DNA
<213> ORGANISM: Artificial sequence
```

```
<220> FEATURE:
<223> OTHER INFORMATION: Oligonucleotide primer

<400> SEQUENCE: 66
gcgaatgatt cagatattca tcac                                         24

<210> SEQ ID NO 67
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 67
tgtattccct cccgtgccac g                                            21

<210> SEQ ID NO 68
<211> LENGTH: 17
<212> TYPE: DNA
<213> ORGANISM: Artificial sequence
<220> FEATURE:
<223> OTHER INFORMATION: Oligonucleotide primer

<400> SEQUENCE: 68
ccagccatgc tcgcggg                                                 17

<210> SEQ ID NO 69
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 69
ggtattccct cccgtgccac g                                            21

<210> SEQ ID NO 70
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 70
aacgaggcaa tggttgttgc                                              20

<210> SEQ ID NO 71
<211> LENGTH: 18
<212> TYPE: DNA
<213> ORGANISM: Artificial sequence
<220> FEATURE:
<223> OTHER INFORMATION: Oligonucleotide primer

<400> SEQUENCE: 71
cagttgctga atccggcg                                                18

<210> SEQ ID NO 72
<211> LENGTH: 18
<212> TYPE: DNA
<213> ORGANISM: Artificial sequence
<220> FEATURE:
<223> OTHER INFORMATION: Oligonucleotide primer

<400> SEQUENCE: 72
gacacctgga cgccatgc                                                18
```

<210> SEQ ID NO 73
<211> LENGTH: 18
<212> TYPE: DNA
<213> ORGANISM: Artificial sequence
<220> FEATURE:
<223> OTHER INFORMATION: Oligonucleotide primer

<400> SEQUENCE: 73
ccacagttcg ctgctgtg                                             18

<210> SEQ ID NO 74
<211> LENGTH: 17
<212> TYPE: DNA
<213> ORGANISM: Artificial sequence
<220> FEATURE:
<223> OTHER INFORMATION: Oligonucleotide primer

<400> SEQUENCE: 74
actggcgctg cgatgtg                                              17

<210> SEQ ID NO 75
<211> LENGTH: 26
<212> TYPE: DNA
<213> ORGANISM: Artificial sequence
<220> FEATURE:
<223> OTHER INFORMATION: Oligonucleotide primer

<400> SEQUENCE: 75
ccagaatttt tcgggttttc acatcc                                    26

<210> SEQ ID NO 76
<211> LENGTH: 17
<212> TYPE: DNA
<213> ORGANISM: Artificial sequence
<220> FEATURE:
<223> OTHER INFORMATION: Oligonucleotide primer

<400> SEQUENCE: 76
tctggcgctg cgatgtg                                              17

<210> SEQ ID NO 77
<211> LENGTH: 18
<212> TYPE: DNA
<213> ORGANISM: Artificial sequence
<220> FEATURE:
<223> OTHER INFORMATION: Oligonucleotide primer

<400> SEQUENCE: 77
cgcactggac aagcgttg                                             18

<210> SEQ ID NO 78
<211> LENGTH: 23
<212> TYPE: DNA
<213> ORGANISM: Artificial sequence
<220> FEATURE:
<223> OTHER INFORMATION: Oligonucleotide primer

<400> SEQUENCE: 78
ttttcgcccc catcagtaaa aac                                       23

<210> SEQ ID NO 79
<211> LENGTH: 21
<212> TYPE: DNA
<213> ORGANISM: Artificial sequence
<220> FEATURE:
<223> OTHER INFORMATION: Oligonucleotide primer

```
<400> SEQUENCE: 79
acaatgccag aacaggccgt g                                              21

<210> SEQ ID NO 80
<211> LENGTH: 19
<212> TYPE: DNA
<213> ORGANISM: Artificial sequence
<220> FEATURE:
<223> OTHER INFORMATION: Oligonucleotide primer

<400> SEQUENCE: 80
acatcgccac accttcggc                                                 19

<210> SEQ ID NO 81
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 81
tgtaagccaa ccgaagaaca a                                              21

<210> SEQ ID NO 82
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 82
cacaatcgtt ctggcgtatt c                                              21

<210> SEQ ID NO 83
<211> LENGTH: 25
<212> TYPE: DNA
<213> ORGANISM: Artificial sequence
<220> FEATURE:
<223> OTHER INFORMATION: Oligonucleotide primer

<400> SEQUENCE: 83
ataagccaac cgaagaacaa aaacg                                          25

<210> SEQ ID NO 84
<211> LENGTH: 22
<212> TYPE: DNA
<213> ORGANISM: Artificial sequence
<220> FEATURE:
<223> OTHER INFORMATION: Oligonucleotide primer

<400> SEQUENCE: 84
gcacaatcgt tctggcgtat tc                                             22

<210> SEQ ID NO 85
<211> LENGTH: 22
<212> TYPE: DNA
<213> ORGANISM: Artificial sequence
<220> FEATURE:
<223> OTHER INFORMATION: Oligonucleotide primer

<400> SEQUENCE: 85
gtgatgaata cgaaactgag cg                                             22

<210> SEQ ID NO 86
```

```
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 86
cacgctcctg attcttcacc                                                   20
```